(12) United States Patent
Hanke et al.

(10) Patent No.: US 8,709,414 B2
(45) Date of Patent: *Apr. 29, 2014

(54) SUPERAGONISTIC ANTI-CD28 ANTIBODIES

(75) Inventors: Thomas Hanke, Veitshoechheim (DE); Martin Trischler, Thuengersheim (DE); Christine Guntermann, Allschwil (CH)

(73) Assignee: TheraMAB LLC., Moscow (RU)

( * ) Notice: Subject to any disclaimer, the term of this patent is extended or adjusted under 35 U.S.C. 154(b) by 96 days.

This patent is subject to a terminal disclaimer.

(21) Appl. No.: 13/269,439

(22) Filed: Oct. 7, 2011

(65) Prior Publication Data

US 2012/0082683 A1 Apr. 5, 2012

Related U.S. Application Data

(60) Continuation of application No. 13/081,866, filed on Apr. 7, 2011, now Pat. No. 8,034,585, which is a division of application No. 12/554,180, filed on Sep. 4, 2009, now Pat. No. 7,939,638, which is a continuation of application No. 11/433,080, filed on May 11, 2006, now Pat. No. 7,585,960.

(60) Provisional application No. 60/680,275, filed on May 11, 2005.

(51) Int. Cl.
*A61K 39/395* (2006.01)

(52) U.S. Cl.
USPC ...................................................... 424/130.1

(58) Field of Classification Search
None
See application file for complete search history.

(56) References Cited

U.S. PATENT DOCUMENTS

| | | | |
|---|---|---|---|
| 7,585,960 B2 | 9/2009 | Hanke et al. | |
| 7,939,638 B2 * | 5/2011 | Hanke et al. | ................ 530/387.1 |
| 2003/0166860 A1 | 9/2003 | Hunig et al. | |
| 2004/0092718 A1 | 5/2004 | Hunig | |

FOREIGN PATENT DOCUMENTS

| | | |
|---|---|---|
| DE | 102 30 223 A1 | 1/2004 |
| EP | 1 600 460 A1 | 11/2005 |
| WO | WO 98/54225 A | 12/1998 |
| WO | WO 03/048194 A2 | 6/2003 |
| WO | WO 03/078468 A2 | 9/2003 |

OTHER PUBLICATIONS

Wadman M., Nature, 2006, 440: 388-389.*
Hopkin M., Nature, 2006, 440: 855-856.*
Mehrishi et al., Vaccine, 2007, 25: 3517-3523.*
Bruggemann et al., "Comparison of the Effector Functions of Human Immunoglobulins Using a Matched Set of Chimeric Antibodies," *J. Exp. Med.* (1987), 166:1351-1361, The Rockefeller University Press.
Hamaguchi et al., "Antibody Isotype-Specific Engagement of Fcγ Receptors Regulates B Lymphocyte Depletion During CD20 Immunotherapy," *J. Exp. Med.* (2006), 203(3):743-753, The Rockefeller University Press.
Isaacs et al., "A Therapeutic Human IgG4 Monoclonal Antibody that Depletes Target Cells in Humans," *Clin. Exp. Immunol.* (1996), 106:427-433, Blackwell Science Ltd.
Nimmerjahn and Ravetch, "Divergent Immunoglobulin G Subclass Activity through Selective Fc Receptor Binding," *Science* (2005), 310:1510-1512.
Nimmerjahn and Ravetch, "Fcγ Receptors: Old Friends and New Family Members," *Immunity* (2006) 24:19-28, Elsevier Inc.
Nimmerjahn et al., "FcγRIV: A Novel FcR with Distinct IgG Subclass Specificity," *Immunity* (2005), 23:41-51, Elsevier Inc.

* cited by examiner

*Primary Examiner* — Ilia Ouspenski
(74) *Attorney, Agent, or Firm* — DLA Piper LLP (US)

(57) ABSTRACT

The present invention relates to one or more nucleic acid(s) encoding a binding molecule specifically binding to a human CD28 molecule, comprising (a) a nucleic acid sequence encoding a VH region and a nucleic acid sequence encoding a VL region comprising CDRs in a human immunoglobulin framework, wherein
  (i) the CDRs of the VH region (CDR-H) comprise the amino acid sequences of SEQ ID NOS: 2 or 18 (CDR-H3), 4 or 20 (CDR-H2) and 6 or 22 (CDR-H1) or are encoded by the nucleic acid sequences of SEQ ID NOS: 1 or 17 (CDR-H3), 3 or 19 (CDR-H2) and 5 or 21 (CDR-H1); and
  (ii) the CDRs of the VL region (CDR-L) comprise the amino acid sequences of SEQ ID NOS: 8 or 24 (CDR-L3), 10 or 26 (CDR-L2) and 12 or 28 (CDR-L1) or are encoded by the nucleic acid sequences of SEQ ID NOS: 7 or 23 (CDR-L3), 9 or 25 (CDR-L2) and 11 or 27 (CDR-L1); and
(b) a nucleic acid sequence encoding the constant region of a human IgG1 or IgG4 antibody.

5 Claims, 17 Drawing Sheets

DNA sequence of HC of TGN1412 including introns, UTRs and leader peptide

```
   1 ggtaccgggc cgacctcacc atgggatgga gctgtatcat cctcttcttg gtagcaacag
  61 ctacaggtaa ggggctcaca gtagcaggct tgaggtctgg acatatatat gggtgacaat
 121 gacatccact ttgcctttct ctccacaggt gtgcattccc aggtgcagct ggtgcagtct
 181 ggggctgagg tgaagaagcc tggggcctca gtgaaggtct cctgcaaggc ttctggatac
 241 accttcacca gctactatat acactgggtg cgacaggccc tggacaagg  gcttgagtgg
 301 attggatgta tttatcctgg aaatgtcaat actaactata tgagaagtt  caaggacagg
 361 gccaccctga ccgtagacac gtccatcagc acagcctaca tggagctgag caggctgaga
 421 tctgacgaca cggccgtgta tttctgtaca agatcacact acggcctcga ctggaacttc
 481 gatgtctggg gccaagggac cacggtcacc gtctcctcag gtgagtcgta cgctagcaag
 541 cttttctgggg caggccgggc ctgactttgg ctgggggcag ggaggggct  aaggtgacgc
 601 aggtggcgcc agccaggtgc acacccaatg cccatgagcc cagacactgg accctgcatg
 661 gaccatcgcg gatagacaag aaccgagggg cctctgcgcc ctgggcccag ctctgtccca
 721 caccgcggtc acatggcacc acctctcttg cagcttccac caagggccca tccgtcttcc
 781 ccctggcgcc ctgctccagg agcacctccg agagcacagc cgccctgggc tgcctggtca
 841 aggactactt ccccgaaccg gtgacggtgt cgtggaactc aggcgccctg accagcggcg
 901 tgcacacctt cccggctgtc ctacagtcct caggactcta ctccctcagc agcgtggtga
 961 ccgtgccctc cagcagcttg ggcacgaaga cctacacctg caacgtagat cacaagccca
1021 gcaacaccaa ggtggacaag agagttggtg agaggccagc acagggaggg agggtgtctg
1081 ctggaagcca ggctcagccc tcctgcctgg acgcaccccg gctgtgcagc cccagcccag
1141 ggcagcaagg catgccccat ctgtctcctc acccggaggc ctctgaccac cccactcatg
1201 ctcagggaga gggtcttctg gatttttcca ccaggctccg ggcagccaca ggctggatgc
1261 ccctacccca ggccctgcgc atacaggggc aggtgctgcg ctcagacctg caagagcca
1321 tatccgggag gaccctgccc ctgacctaag cccaccccaa aggccaaact ctccactccc
1381 tcagctcaga caccttctct cctcccagat ctgagtaact cccaatcttc tctctgcaga
1441 gtccaaatat ggtccccccat gcccatcatg cccaggtaag ccaacccagg cctcgccctc
1501 cagctcaagg cgggacaggt gccctagagt ggcctgcatc cagggacagg ccccagccgg
1561 gtgctgacgc atccacctcc atctcttcct cagcacctga gttcctgggg ggaccatcag
1621 tcttcctgtt cccccccaaaa cccaaggaca ctctcatgat ctcccggacc cctgaggtca
1681 cgtgcgtggt ggtggacgtg agccaggaag acccccgaggt ccagttcaac tggtacgtgg
1741 atggcgtgga ggtgcataat gccaagacaa agccgcggga ggagcagttc aacagcacgt
1801 accgtgtggt cagcgtcctc accgtcctgc accaggactg gctgaacggc aaggagtaca
1861 agtgcaaggt ctccaacaaa ggcctcccgt cctccatcga gaaaaccatc tccaaagcca
1921 aaggtgggac ccacggggtg cgagggccac atggacagag gtcagctcgg cccaccctct
1981 gccctggag tgaccgctgt gccaacctct gtccctacag ggcagccccg agagccacag
2041 gtgtacaccc tgcccccatc caggaggag atgaccaaga accaggtcag cctgacctgc
2101 ctggtcaaag gcttctaccc cagcgacatc gccgtggagt gggagagcaa tgggcagccg
2161 gagaacaact acaagaccac gcctcccgtg ctggactccg acggctcctt cttcctctac
2221 agcaggctaa ccgtggacaa gagcaggtgg caggagggga atgtcttctc atgctccgtg
2281 atgcatgagg ctctgcacaa ccactacaca cagaagagcc tctccctgtc tctgggtaaa
2341 tgagtgccag ggccggcaag cccccgctcc ccgggctctc ggggtcgcgc gaggatgctt
2401 ggcacgtacc ccgtctatact acttcccagg cacccagcat ggaaataaag cacccaccac
2461 tgccctgggc cctgtgaga ctgtgatggt tctttccacg ggtcaggccg agtctgaggc
2521 ctgagtgaca tgagggaggc agagcggatc c
```

Pos. 21 atg: 1. leader codon   Pos. 157 tcc: last leader codon (leader with intron!)

Pos. 160 cag: 1. VHR codon   Pos. 517 tca: last VHR codon

Pos. 2338 aaa : last IgG4-const. codon

Pos. 2341 tga: STOP

FIGURE 1

AS sequence of HC of TGN1412 including leader peptide

MGWSCIILFLVATATGVHS<u>Q</u>VQLVQSGAEVKKPGASVKVSCKASGYTFTSYYIHWVRQAPGQ

GLEWIGCIYPGNVNTNYNEKFKDRATLTVDTSISTAYMELSRLRSDDTAVYFCTRSHYGLDW

NFDVWGQGTTVTVS<u>S</u>ASTKGPSVFPLAPCSRSTSESTAALGCLVKDYFPEPVTVSWNSGALT

SGVHTFPAVLQSSGLYSLSSVVTVPSSSLGTKTYTCNVDHKPSNTKVDKRVESKYGPPCPSC

PAPEFLGGPSVFLFPPKPKDTLMISRTPEVTCVVVDVSQEDPEVQFNWYVDGVEVHNAKTKP

REEQFNSTYRVVSVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGSFFLYSRLTVDKS

RWQEGNVFSCSVMHEALHNHYTQKSLSLSLGK

Observed variants at the C terminus during expression of CHO cells:

(...) SLGK or (...) SLG

Leader peptide

MGWSCIILFLVATATGVHS

FIGURE 2

DNA sequence of LC of TGN1412 including introns, UTRs and leader peptide

```
   1 ggtaccgggc cgacctcacc atgggatgga gctgtatcat cctcttcttg gtagcaacag
  61 ctacaggtaa ggggctcaca gtagcaggct tgaggtctgg acatatatat gggtgacaat
 121 gacatccact ttgcctttct ctccacaggt gtgcattccg acatccagat gacccagtct
 181 ccatcctccc tgtctgcatc tgtaggagac agagtcacca tcacttgcca tgccagtcaa
 241 aacatttatg tttggttaaa ctggtatcag cagaaaccag ggaaagcccc taagctcctg
 301 atctataagg cttccaacct gcacacaggg gtcccatcaa ggttcagtgg cagtggatct
 361 gggacagatt tcactctcac catcagcagt ctgcaacctg aagattttgc aacttactac
 421 tgtcaacagg tcaaactta tccgtacacg ttcggcggag ggaccaaggt ggagatcaaa
 481 cgtgagtcgt acgctagcaa gcttgatatc gaattctaaa ctctgagggg gtcggatgac
 541 gtggccattc tttgcctaaa gcattgagtt tactgcaagg tcagaaaagc atgcaaagcc
 601 ctcagaatgg ctgcaaagag ctccaacaaa acaatttaga actttattaa ggatagggg
 661 gaagctagga agaaactcaa acatcaagat ttttaaatac gcttcttggt ctccttgcta
 721 taattatctg ggataagcat gctgttttct gtctgtccct aacatgccct gtgattatcc
 781 gcaaacaaca cacccaaggg cagaactttg ttacttaaac accatcctgt ttgcttcttt
 841 cctcaggaac tgtggctgca ccatctgtct tcatcttccc gccatctgat gagcagttga
 901 aatctggaac tgcctctgtt gtgtgcctgc tgaataactt ctatcccaga gaggccaaag
 961 tacagtggaa ggtggataac gccctccaat cgggtaactc ccaggagagt gtcacagagc
1021 aggacagcaa ggacagcacc tacagcctca gcagcaccct gacgctgagc aaagcagact
1081 acgagaaaca caaagtctac gcctgcgaag tcacccatca gggcctgagc tcgcccgtca
1141 caaagagctt caacagggga gagtgttaga gggagaagtg cccccacctg ctcctcagtt
1201 ccagcctgac cccctcccat cctttggcct ctgacccttt tccacaggg gacctacccc
1261 tattgcggtc ctccagctca tctttcacct cacccccctc ctcctccttg gctttaatta
1321 tgctaatgtt ggaggagaat gaataaataa agtgaatctt gcacctgtg gtttctctct
1381 ttcctcattt aataattatt atctgttgtt ttaccaacta ctcaatttct cttataaggg
1441 actaaatatg tagtcatcct aaggcgcata accatttata aaaatcatcc ttcattctat
1501 tttaccctat catcctctgc aagacagtcc tccctcaaac ccacaagcct tctgtcctca
1561 cagtcccctg ggccatggta ggagagactt gcttccttgt tttcccctcc tcagcaagcc
1621 ctcatagtcc tttttaaggg tgacaggtct tacagtcata tatcctttga ttcaattccc
1681 tgagaatcaa ccaaagcaaa ttcctgcagc ccggggggatc c
```

Pos. 21 atg: 1. leader codon   Pos. 157 tcc: last leader codon
(leader with intron!)

Pos. 160 gac: 1. VLR codon   Pos. 478 aaa: last VLR codon

Pos. 1164 tgt : last Kappa-const. codon

Pos. 1167 tag: STOP

FIGURE 3

AS sequence of LC of TGN1412 including leader peptide

MGWSCIILFLVATATGVHS<u>D</u>IQMTQSPSSLSASVGDRVTITCHASQNIYVWLNWYQQKPGKA
PKLLIYKASNLHTGVPSRFSGSGSGTDFTLTISSLQPEDFATYYCQQGQTYPYTFGGGTKVE
I<u>K</u>RTVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC

Leader peptide

MGWSCIILFLVATATGVHS

FIGURE 4

DNA sequence of HC of TGN1112 including introns, UTRs and leader peptide

```
   1 ggtaccgggc cgacctcacc atgggatgga gctgtatcat cctcttcttg gtagcaacag
  61 ctacaggtaa ggggctcaca gtagcaggct tgaggtctgg acatatatat gggtgacaat
 121 gacatccact ttgcctttct ctccacaggt gtgcattccc aggtgcagct ggtgcagtct
 181 ggggctgagg tgaagaagcc tggggcctca gtgaaggtct cctgcaaggc ttctggatac
 241 accttcacca gctactatat acactgggtg cgacaggccc ctggacaagg gcttgagtgg
 301 attggatgta tttatcctgg aaatgtcaat actaactata atgagaagtt caaggacagg
 361 gccaccctga ccgtagacac gtccatcagc acagcctaca tggagctgag caggctgaga
 421 tctgacgaca cggccgtgta tttctgtaca agatcacact acggcctcga ctggaacttc
 481 gatgtctggg gccaagggac cacggtcacc gtctcctcag gtgagtcgta cgctagcaag
 541 ctttctgggg caggccaggc ctgaccttgg ctttggggca gggagggggc taaggtgagg
 601 caggtggcgc cagccaggtg cacacccaat gcccatgagc cagacactg gacgctgaac
 661 ctcgcggaca gttaagaacc cagggcctc tgcgccctgg gcccagctct gtcccacacc
 721 gcggtcacat ggcaccacct ctcttgcagc ctccaccaag ggcccatcgg tcttcccct
 781 ggcaccctcc tccaagagca cctctggggg cacagcggcc ctgggctgcc tggtcaagga
 841 ctacttcccc gaaccggtga cggtgtcgtg gaactcaggc gccctgacca gcggcgtgca
 901 caccttcccg gctgtcctac agtcctcagg actctactcc ctcagcagcg tggtgaccgt
 961 gccctccagc agcttgggca cccagaccta catctgcaac gtgaatcaca agcccagcaa
1021 caccaaggtg gacaagaaag ttggtgagag gccagcacag ggagggaggg tgtctgctgg
1081 aagccaggct cagcgctcct gcctggacgc atcccggcta tgcagcccca gtccagggca
1141 gcaaggcagg ccccgtctgc ctcttcaccc ggaggcctct gcccgcccca ctcatgctca
1201 gggagagggt cttctggctt tttcccaggc tctgggcagg cacaggctag gtgcccctaa
1261 cccaggccct gcacacaaag gggcaggtgc tgggctcaga cctgccaaga gccatatccg
1321 ggaggaccct gccccctgacc taagcccacc ccaaaggcca aactctccac tccctcagct
1381 cggacacctt ctctcctccc agattccagt aactcccaat ctttctctg cagagcccaa
1441 atcttgtgac aaaactcaca catgcccacc gtgcccaggt aagccagccc aggcctcgcc
1501 ctccagctca aggcgggaca ggtgccctag agtagcctgc atccagggac aggccccagc
1561 cgggtgctga cacgtccacc tccatctctt cctcagcacc tgaactcctg ggggaccgt
1621 cagtcttcct cttccccca aaacccaagg acaccctcat gatctcccgg acccctgagg
1681 tcacatgcgt ggtggtggac gtgagccacg aagaccctga ggtcaagttc aactggtacg
1741 tggacggcgt ggaggtgcat aatgccaaga caaagccgcg ggaggagcag tacaacagca
1801 cgtaccgggt ggtcagcgtc ctcaccgtcc tgcaccagga ctggctgaat ggcaaggagt
1861 acaagtgcaa ggtctccaac aaagccctcc cagcccccat cgagaaaacc atctccaaag
1921 ccaaaggtgg gacccgtggg gtgcgagggc cacatggaca gaggccggct cggcccaccc
1981 tctgccctga gagtgaccgc tgtaccaacc tctgtcccta cagggcagcc ccgagaacca
2041 caggtgtaca ccctgccccc atcccgggat gagctgacca gaaccaggt cagcctgacc
2101 tgcctggtca aaggcttcta tcccagcgac atcgccgtgg agtgggagag caatgggcag
2161 ccggagaaca actacaagac cacgcctccc gtgctggact ccgacggctc cttcttcctc
2221 tacagcaagc tcaccgtgga caagagcagg tggcagcagg ggaacgtctt ctcatgctcc
2281 gtgatgcatg aggctctgca caaccactac acgcagaaga gcctctccct gtctccgggt
2341 aaatgagtgc gacggccggc aagcccccgc tccccgggct ctgcggtcg cacgaggatg
2401 cttggcacgt accccctgta catacttccc gggcgcccag catggaaata aagcacccag
2461 cgctgccctg ggccctgcg agactgtgat ggttctttcc acgggtcagg ccgagtctga
2521 ggcctgagtg gcatgaggga ggcagagcgg gtc
```

Pos. 21 atg: 1. leader codon    Pos. 157 tcc: last leader codon
(leader with intron!)

Pos. 160 cag: 1. VHR codon    Pos. 517 tca: last VHR codon

Pos. 2341 aaa : last IgG1-const. codon

Pos. 2344 tga: STOP

FIGURE 5

AS sequence of HC of TGN1112 including leader peptide

MGWSCIILFLVATATGVHSQVQLVQSGAEVKKPGASVKVSCKASGYTFTSYYIHWVRQAPGQ

GLEWIGCIYPGNVNTNYNEKFKDRATLTVDTSISTAYMELSRLRSDDTAVYFCTRSHYGLDW

NFDVWGQGTTVTVSSASTKGPSVFPLAPSSKSTSGGTAALGCLVKDYFPEPVTVSWNSGALT

SGVHTFPAVLQSSGLYSLSSVVTVPSSSLGTQTYICNVNHKPSNTKVDKKVEPKSCDKTHTC

PPCPAPELLGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDSDGSFFLYSKLTV

DKSRWQQGNVFSCSVMHEALHNHYTQKSLSLSPGK leader peptide

MGWSCIILFLVATATGVHS

FIGURE 6

DNA sequence of LC of TGN1112 including introns, UTRs and leader peptide

```
   1 ggtaccgggc cgacctcacc atgggatgga gctgtatcat cctcttcttg gtagcaacag
  61 ctacaggtaa ggggctcaca gtagcaggct tgaggtctgg acatatatat gggtgacaat
 121 gacatccact ttgcctttct ctccacaggt gtgcattccg acatccagat gacccagtct
 181 ccatcctccc tgtctgcatc tgtaggagac agagtcacca tcacttgcca tgccagtcaa
 241 aacatttatg tttggttaaa ctggtatcag cagaaaccag ggaaagcccc taagctcctg
 301 atctataagg cttccaacct gcacacaggg gtcccatcaa ggttcagtgg cagtggatct
 361 gggacagatt tcactctcac catcagcagt ctgcaacctg aagatttgc aacttactac
 421 tgtcaacagg gtcaaactta tccgtacacg ttcggcggag ggaccaaggt ggagatcaaa
 481 cgtgagtcgt acgctagcaa gcttgatatc gaattctaaa ctctgagggg gtcggatgac
 541 gtggccattc tttgcctaaa gcattgagtt tactgcaagg tcagaaaagc atgcaaagcc
 601 ctcagaatgg ctgcaaagag ctccaacaaa acaatttaga actttattaa ggaataggggg
 661 gaagctagga agaaactcaa aacatcaaga ttttaaatac gcttcttggt ctccttgcta
 721 taattatctg ggataagcat gctgttttct gtctgtccct aacatgccct gtgattatcc
 781 gcaaacaaca cacccaaggg cagaactttg ttacttaaac accatcctgt ttgcttcttt
 841 cctcaggaac tgtggctgca ccatctgtct tcatcttccc gccatctgat gagcagttga
 901 aatctggaac tgcctctgtt gtgtgcctgc tgaataactt ctatcccaga gaggccaaag
 961 tacagtggaa ggtggataac gccctccaat cgggtaactc ccaggagagt gtcacagagc
1021 aggacagcaa ggacagcacc tacagcctca gcagcaccct gacgctgagc aaagcagact
1081 acgagaaaca caaagtctac gcctgcgaag tcacccatca gggcctgagc tcgcccgtca
1141 caaagagctt caacagggga gagtgttaga gggagaagtg cccccacctg ctcctcagtt
1201 ccagcctgac ccctcccat cctttggcct ctgaccctt ttccacaggg gacctacccc
1261 tattgcggtc ctccagctca tctttcacct cacccccctc ctcctccttg ctttaatta
1321 tgctaatgtt ggaggagaat gaataaataa agtgaatctt gcacctgtg gtttctctct
1381 ttcctcattt aataattatt atctgttgtt ttaccaacta ctcaatttct cttataaggg
1441 actaaatatg tagtcatcct aaggcgcata accatttata aaaatcatcc ttcattctat
1501 tttaccctat catcctctgc aagacagtcc tcctcaaac ccacaagcct tctgtcctca
1561 cagtcccctg ggccatggta ggagagactt gcttccttgt tttcccctcc tcagcaagcc
1621 ctcatagtcc tttttaaggg tgacaggtct tacagtcata tatcctttga ttcaattccc
1681 tgagaatcaa ccaaagcaaa ttcctgcagc ccggggggatc c
```

Pos. 21 atg: 1. leader codon   Pos. 157 tcc: last leader codon
(leader with intron!)

Pos. 160 gac: 1. VLR codon   Pos. 478 aaa: last VLR codon

Pos. 1164 tgt : last Kappa-const. codon

Pos. 1167 tag: STOP

FIGURE 7

AS sequence of LC of TGN1112 including leader peptide

MGWSCIILFLVATATGVHS<u>D</u>IQMTQSPSSLSASVGDRVTITCHASQNIYVWLNWYQQKPGKA

PKLLIYKASNLHTGVPSRFSGSGSGTDFTLTISSLQPEDFATYYCQQGQTYPYTFGGGTKVE

I<u>K</u>RTVAAPSVFIFPPSDEQLKSGTASVVCLLNNFYPREAKVQWKVDNALQSGNSQESVTEQD

SKDSTYSLSSTLTLSKADYEKHKVYACEVTHQGLSSPVTKSFNRGEC leader peptide

MGWSCIILFLVATATGVHS

FIGURE 8

VRLC of TGN1112/TGN1412:

| CDR definition according to | Abm/Kabat combi | Kabat |
|---|---|---|
| CDR-L1 | HASQNIYVWLN | HASQNIYVWLN |
| CDR-L2 | KASNLHT | KASNLHT |
| CDR-L3 | QQGQTYPYT | QQGQTYPYT |

With regard to the VRLC, the CDRs are defined the same according to both systems.

VRHC of TGN1112/TGN1412:

| CDR definition according to | Abm/Kabat combi | Kabat |
|---|---|---|
| CDR-H1 | GYTFTSYYIH | SYYIH |
| CDR-H2 | CIYPGNVNTNYNEKFKD | CIYPGNVNTNYNEKFKD |
| CDR-H3 | SHYGLDWNFDV | SHYGLDWNFDV |

FIGURE 17

SUPERAGONISTIC ANTI-CD28 ANTIBODIES

CROSS REFERENCE TO RELATED APPLICATIONS

This application is a continuation application of U.S. application Ser. No. 13/081,866 filed Apr. 7, 2011, now issued as U.S. Pat. No. 8,034,585; which is a divisional application of U.S. application Ser. No. 12/554,180 filed Sep. 4, 2009, now issued as U.S. Pat. No. 7,939,638; which is a continuation application of U.S. application Ser. No. 11/433,080 filed May 11, 2006, now issued as U.S. Pat. No. 7,585,960; which claims the benefit under 35 USC §119(e) to U.S. Application Ser. No. 60/680,275 filed May 11, 2005, now expired. The disclosure of each of the prior applications is considered part of and is incorporated by reference in the disclosure of this application.

BACKGROUND OF THE INVENTION

1. Field of the Invention

The invention relates to one or more nucleic acids encoding a binding molecule specifically binding a human CD28 molecule, comprising (a) a nucleic acid sequence encoding a VH region and a nucleic acid sequence encoding a VL region comprising CDRs in a human immunoglobulin framework, wherein
  (i) the CDRs of the VH region (CDR-H) comprise the amino acid sequences of SEQ ID NOS: 2 or 18 (CDR-H3), 4 or 20 (CDR-H2) and 6 or 22 (CDR-H1) or are encoded by the nucleic acid sequences of SEQ ID NOS: 1 or 17 (CDR-H3), 3 or 19 (CDR-H2) and 5 or 21 (CDR-H1); and
  (ii) the CDRs of the VL region (CDR-L) comprise the amino acid sequences of SEQ ID NOS: 8 or 24 (CDR-L3), 10 or 26 (CDR-L2) and 12 or 28 (CDR-L1) or are encoded by the nucleic acid sequences of SEQ ID NOS: 7 or 23 (CDR-L3), 9 or 25 (CDR-L2) and 11 or 27 (CDR-L1); and
(b) a nucleic acid sequence encoding a constant region of a human IgG1 or IgG4 antibody.

2. Background Information

In the description a number of prior art documents including patent applications and manufacturer's instructions for use are mentioned. Whereas the disclosure content of these documents is not considered to be relevant for the patentability of the present invention, it is incorporated by reference into the present description.

The stimulation of resting T lymphocytes for activation, proliferation and functional differentiation requires the occupancy of two surface structures, so-called receptors: 1. of the antigen receptor having a different specificity from cell to cell and being necessary for the recognition of antigens, e.g. viral decomposition products; as well as 2. the CD28 molecule equally expressed on all resting T cells with the exception of a subgroup of the human CD8-T cells, the CD28 molecule naturally binding to ligands on the surface of other cells of the immune system. This is also called costimulation of the antigen-specific immune reaction by CD28. In cell culture, these processes can be simulated by occupancy of the antigen receptor as well as of the CD28 molecule with suitable monoclonal antibodies (mAb). In the classic system of costimulation neither the occupancy of the antigen receptor nor that of the CD28 molecule alone leads to T cell proliferation, however, the occupancy of both receptors is effective. This observation was made on T cells of the human, the mouse and the rat.

However, there are also known CD28-specific monoclonal antibodies (mAb) which may trigger T cell proliferation without costimulation. Such a superagonistic, i.e. the activation of resting T lymphocytes by CD28-specific mAb independent of the occupancy of the antigen receptor, is known for example from Tacke at al., Eur. J. Immunol. 1997, 27:239-247. This publication described two kinds of CD28 specific monoclonal antibodies having differing functional properties: costimulatory mAb which costimulate the activation of resting T cells only in case the antigen receptor is simultaneously occupied, and superagonistic mAb which can activate in vitro and in rats T lymphocytes of all classes to proliferate without occupying the antigen receptor.

Superagonistic monoclonal antibodies with specificity to the human CD28 molecule, which very efficiently activate and expand T cells in vitro without stimulation of the T cell antigen receptor (TCR), are further known from DE 101 60 516.1 as well as from Luhder et al., J. Exp. Med., 2003, 197: 955-966. However, in this work immobilized antibodies were used, which, as shown further below, are not suitable for therapeutic use.

Furthermore, superagonistic anti-CD28 antibodies showed pronounced anti-inflammatory properties in animal models and in cell culture. Thus, for example, as documented by Schmidt et al., J. Neuroimmunol. 2003, 140: 143-152, the application of a superagonistic monoclonal antibody against the CD28 molecule of the rat may prevent the development of an inflammatory peripheral neuropathy, the Experimental Autoimmune Neuritis (EAN). From DE 102 12 108.7 as well as from Lin et al., Eur. J. Immunol., 2003, 33:626-638 it is known that superagonistic anti-CD28 antibodies may cause a superproportionally strong activation of regulatory T cells. The function of regulatory T cells is to control autoaggressive T cells and to make sure that generally no excessive inflammatory reaction develops (Schwartz, Nature Immunol., 2005, 6: 327-330). However, an intervention in CD28-mediated costimulation may shift the Th1/Th2 balance in favour of the pro-inflammatory Th1 phenotype and thus harbours the risk of aggravating autoimmune/inflammatory reactions (see Schmidt et al., supra).

For obvious reasons it is desirable that therapeutic antibody candidates prevent immunogenicity, i.e. triggering an immune response against the active substance, with the aim of fully exploiting the pharmacological activity in humans and simultaneously reducing undesirable side effects. In order to prevent the immunogenicity of not human-derived antibodies, for example, the "humanization" of antibodies by means of genetic engineering technology is state of the art. Here the antigen-binding site of an antibody originally not human-derived is conserved, while the rest of the antibody molecule, in particular the constant portions of the antibodies (constant domain or Fc fragment), is exchanged against a structurally related variant from the human genome (Hwang et al., Methods, 2005, 36:3-10).

As known from DE 102 30 223.5, the crosslinking of superagonistic anti-human CD28 antibodies enhances their ability to activate T lymphocytes in a cell suspension. For example, the proliferation of purified T lymphocytes is many times stronger when superagonistic antibodies are used in form of immobilized molecule complexes on paramagnetic beads instead of being present in soluble form in the T cell suspension. For galenical use in humans, the application of such complexed dosage forms of superagonistic anti-CD28 antibodies is, however, not possible for obvious reasons. Furthermore, in DE 102 30 223.5 anti-mouse-IgG antibodies immobilized on paramagnetic beads were used as crosslinking agent. In this respect, too, an analogous approach for a therapeutic application in humans is out of the question, since the use of anti-human-IgG antibodies has to be ruled out in view of the large number of cross-reactions to be expected. Last but not least, the approach described in DE 102 30 223.5 is limited to an in-vitro method wherein purified T cells are used. For the development of therapeutic superagonistic anti-CD28 antibodies it had therefore to be checked whether there exists a suitable antibody format which allows in vivo a sufficient crosslinking but does not lead to undesirable effects.

It is known that a natural recognition and crosslinking of Fc domains of antibodies in the human body are mediated by Fc receptors that are expressed on various cell types (Woof et al., Nature Reviews Immunol., 2004, 1-11). The aim of the Fc receptor-mediated antibody binding in a physiological context is the "removal" or destruction of antibody-occupied cells, since it must be assumed that antibodies are only formed against such cells that are derived from foreign tissue, that are bacterially or virally infected, are subject to stress or are malignantly degenerated. Important Fc receptor-mediated mechanisms for eliminating antibody-loaded cells are complement-dependent cytotoxicity (CDC), antibody-dependent cellular cytotoxicity (ADCC) and opsonization, i.e. marking for phagocytosis by specialized phagocytes.

The Fc receptors responsible for the recognition of Fc domains of human antibodies of the IgG isotype may be classified into the groups CD64 (Fc gamma receptor I; high-affinity receptor); CD32 (Fc gamma receptor II; intermediate-affinity receptor) and CD16 (Fc gamma receptor III; low-affinity receptor). Their binding properties to antibodies of the IgG subgroups IgG1, IgG2, IgG3 and IgG4 as well as the effector functions triggered by the binding to these antibodies are known to a large extent (Woof et al., Nature Reviews Immunol., 2004, 1-11). Thus, the stimulation of Fc receptors binding to IgG1 or IgG4 (CD64 binds strongly to IgG1, moderately to IgG4; CD32 weakly to IgG1, not to IgG4; CD16b strongly to IgG1, very weakly or not at all to IgG4) generally also causes elimination of the target cells via ADCC or CDC.

SUMMARY OF THE INVENTION

In summary, it is thus known from the prior art that crosslinking if caused by molecules present in the human body mostly is accompanied by the elimination of antibody-loaded cells.

Thus, the object in the development of therapeutic super-agonistic anti-CD28 antibodies consisted in finding an antibody format that can on the one hand be cross-linked in the body by physiologically available structures or molecules, such as Fc receptors. On the other hand, such crosslinking must not lead to a(n) (significant) elimination or destruction of the actual target structure of the antibody, namely the CD28+ T cells. This object is achieved by the embodiments provided in the claims.

Thus, the invention relates to one or more nucleic acids encoding a binding molecule specifically binding to a human CD28 molecule, comprising
  (a) a nucleic acid sequence encoding a VH region and a nucleic acid sequence encoding a VL region comprising CDRs in a human immunoglobulin framework, wherein
    (i) the CDRs of the VH region (CDR-H) comprise the amino acid sequences of SEQ ID NOS: 2 or 18 (CDR-H3), 4 or 20 (CDR-H2) and 6 or 22 (CDR-H1) or are encoded by the nucleic acid sequences of SEQ ID NOS: 1 or 17 (CDR-H3), 3 or 19 (CDR-H2) and 5 or 21 (CDR-H1); and
    (ii) the CDRs of the VL region (CDR-L) comprise the amino acid sequences of SEQ ID NOS: 8 or 24 (CDR-L3), 10 or 26 (CDR-L2) and 12 or 28 (CDR-L1) or are encoded by the nucleic acid sequences of SEQ ID NOS: 7 or 23 (CDR-L3), 9 or 25 (CDR-L2) and 11 or 27 (CDR-L1); and
  (b) a nucleic acid sequence encoding a constant region of a human IgG1 or IgG4 antibody.

The term "nucleic acid" in the context of the present invention relates to one or more nucleic acid molecules which in toto encode the binding molecule according to the present invention. The encoding regions for the components of the binding molecule according to the present invention may thus be comprised on one nucleic acid molecule or be found on two or more than two distinct nucleic acid molecules. In particular, the encoding regions for the $V_H$ region and the constant region of the heavy chain of the human IgG1 or IgG4 may be found on one nucleic acid molecule and the $V_L$ region and the constant region of the light chain of the IgG1 or IgG4 on a second nucleic acid molecule. The constant region of the light chain may correspond both to the sequence of a κ gene and that of a λ gene encoding the constant regions of human light chains. According to the present invention, the $V_H$ region, or, respectively, the $V_L$ region in the binding molecule encoded by the nucleic acid(s) according to the present invention is operatively linked with the constant region, as is the case for example in an antibody. Likewise, it shall be understood that the encoded (poly)peptide chain(s) after synthesis fold or assemble in such a way that the $V_H$ region and the $V_L$ region come into close proximity and form an antigen-binding site. This, too, is exemplified by an antibody.

The term "comprise" shall mean on the one hand "contain" (besides other objects) and on the other hand "consisting of" (without including further objects).

The CD-28 molecule is, as described above, a transmembrane molecule that is expressed as homodimer on the surface of T cells. The amino acid sequence of human CD28 may be accessed under GenBank Accession No. NM_006139.

The term "superagonistic" as used in the context of the present invention describes a property of the binding molecules according to the present invention, which by specifically binding to/interacting with a particular epitope of the CD28 molecule enable an antigen-receptor independent activation of lymphocytes. Thus, a "superagonistic stimulation" corresponds to the activation of $CD28^+$ T cells without that a costimulation, i.e. a further binding event besides binding/interacting of the CD28-specific antibody is necessary for the stimulation of proliferation. Such an activation may inter alia be shown via a detection of activation markers on the cells, the induction of transcription factors, proliferation or the expression or secretion of cytokines.

The activation and/or expansion of T cells means in particular the augmentation of the metabolic activity, the augmentation of the cell volume, the synthesis of immunologically important molecules, such as CD71 or CD25, and initiation of cell division (proliferation) in response to a stimulus from outside. Preferably, after activation or expansion as a result there exist more T cells than before.

The terms "$V_H$ region" and "$V_L$ region" are well-known to the person skilled in the art and describe in the prior art the amino-terminal domain of an antibody, which results from recombination of the V-, D- and J-gene segments during B lymphocyte maturation. The variable regions of the heavy and the light chain of antibodies are responsible for the specific binding/interaction of an antibody to/with its specific epitope (cf. Haseman and Capra "Immunoglobulins: Structure and Function", in "Fundamental Immunology" (ed. W. E.

Paul), Raven Press, New York, 2$^{nd}$ edition 1989). Via recombinant techniques, the V$_H$ and V$_L$ regions may also be combined with other structures than the naturally occurring C regions.

The term "CDR" (complementary determining regions) describes complementary determining regions of the receptors of the immune system, in particular of antibodies and T cell receptors. These are known to the person skilled in the art as regions of a receptor which contact the ligand and determine the specificity of the receptor. The CDRs are the most variable parts of the receptors and responsible for their variety. Examples of such receptors comprise antibodies. Three loops each are found on the distal ends of the two variable regions of antibodies. These are generally numbered serially from CDR-H1 to CDR-H3 on the heavy chain and CDR-L1 to CDR-L3 on the light chain of antibodies.

The amino acid sequence of one or more CDRs can be determined by the skilled person from a known amino acid sequence of an antibody, antibody fragment or derivative. The above mentioned CDRs have been determined according to the modified Kabat method (AbM/Kabat combi). This method can be derived inter alia from the rules "How to identify the CDRs by looking at a sequence" at the homepage of Andrew C. R. Martin (http://www.bioinf.org.uk/abs/). Alternatively, according to the present invention rules for determining/detecting the CDRs of the described binding molecules according to Kabat may be used (see Kabat, E. A., et al., 1991; *Sequences of Proteins of Immunological Interest*, Fifth Edition, NIH Publication No. 91-3242, as well as Johnson, G. and Wu, T. T. 2000, Nucleic Acids Research). In the present case, in the embodiments of the present invention, there have been used the CDR sequences determined according to the method of Kabat and shown in FIG. 17 as well as emphasized in FIGS. 2 and 6. This also means that the framework regions slightly change without, however, it being necessary that the overall sequence of the binding molecule changes or would have to change. As already mentioned: The CDRs of the binding molecules of the present invention according to the Kabat system as well as according to the AbM/Kabat combi system are shown in FIG. 17. For example, the CDR-H1 sequence according to the modified Kabat system is shown by the sequence GYTFTSYYIH, the one according to the traditional Kabat method by SYYIH.

The term "human immunogobulin framework" describes the entirety of those amino acid sequence sections in the folded state which lie in the variable region of a human antibody between the CDRs as well as the N- and C-terminus thereof and define the spatial framework (steric formation) of the immunoglobulin.

The term "constant region" is known to the person skilled in the art inter alia from Janeway and Travers (Immunologie, 2$^{nd}$ Edition, Spektrum Akademischer Verlag, see also reference W. E. Paul, supra). Human antibodies of the IgG isotype comprise the subclasses IgG1, IgG2, IgG3 and IgG4. According to the invention, a constant region of a human IgG1 or IgG4 antibody is used in the binding molecules. The term "binding to/interacting with" in the context of the present invention is defined as binding/interaction of an "antigen-binding site" with an epitope. The term "antigen-binding site" defines, in accordance with the present invention, a motif of a polypeptide/binding molecule that is suitable to interact with a specific antigen or a group of antigens. Such specific binding/interaction is also defined as "specific recognition" of an antigen. According to the present invention, the specific recognition of an antigen means a specific binding to/interaction with at least two, preferably three, more preferably at least four amino acids of one antigen. The part of the antigen that undergoes the binding/interaction with the antigen-binding site is called epitope. The antigen for the binding molecules according to the present invention is the CD28 molecule. The epitope of the binding molecules of the present invention is found on the section of the CD28 molecule called CD loop. This specific binding/interaction leads to the induction of a superagonistic signal (activation/stimulation) in a CD28$^+$ cell. A specific binding/interaction can also be described by the "lock-and-key principle". Specific motifs in an amino acid sequence of the antigen recognition site and of the antigen bind to each other due to their primary, secondary or tertiary structure.

The term "specific interaction" shall mean in the context of the present invention that the binding molecule does not cross-react or not to a significant extent with (poly)peptides having a structure similar to the specifically recognized antigen and being expressed on the same cells. The cross-reactivity of a group of binding molecules may, for example, be analysed by determining the binding properties/binding strengths under usual conditions (see inter alis Harlow and Lane, Antibodies: A Laboratory Manual, Cold Spring Harbor Laboratory Press, 1988 and Using Antibodies: A Laboratory Manual, Cold Spring Harbor Laboratory Press, 1999). Explicitly comprised by the definition of the "binding to/interacting with" are also conformational epitopes, structural epitopes and discontinuous epitopes that are assembled from two or more regions of an antigen (residues of different regions of one or more polypeptide chains) and combine to a "natural epitope" (see Sela, (1969) Science 166, 1365 and Layer, (1990) Cell 61, 553-6).

The term "crosslinking" describes creating a spatial proximity of several binding molecules which are bound to the specific antigen/interact with the specific antigen, which results in a multivalent binding of the target molecule (specific epitope) CD28. For the binding molecules according to the present invention, crosslinking via the F$_c$ fragment of the humanized IgG antibody is preferred. This can be achieved e.g. by binding this fragment to the F$_c$ receptors on lymphocytes or other cells. Binding molecules according to the present invention (encoded by nucleic acids according to the present invention) have the surprising property that CD28$^+$ cells can be activated/stimulated by cross-linked binding molecules without being eliminated.

The term "binding molecule" is used in the context of the present invention to describe a group of molecules which may be in the form of monomers or also of dimers, trimers or oligomers. Dinners, trimers or oligomers may be homomers as well as heteromers. Preferably, the individual chains of dimers, trimers or oligomers are covalently linked. Particularly preferred are covalent linkages via disulfide bridges. Alternatively, the dimers, trimers or oligomers may also be linked with each other via non-covalent interactions. Corresponding dimerizations, trimerizations or oligomerizations may be effected for example by interactions of specific sequence motifs in the individual molecules. An example for such intrinsic interaction is the interaction of monomers by a leucin-zipper motif leading to dimerization.

The mouse-anti-human CD28 antibody 5.11A1 described in Luhder et al., J. Exp. Med., 2003, 197: 955-966 served as starting point for the superagonistic CD28 binding molecules according to the present invention. The variable regions of the heavy and the light chain of the 5.11A1 antibody were humanized by genetic engineering techniques of the prior art. This technology is inter alia known to the skilled person as "CDR grafting" (see P. T. Jones et al. 1986, Nature 321: 522-526 as well as Ewert et al., 2004, Methods, 34: 184-199).

The humanized variable regions were fused with the constant region of human antibodies of the IgG isotype.

It is known that in principle all IgG isotypes (IgG1-4) are suitable for therapeutic use. As is known, the large majority of the antibodies in therapeutic development have a neutralizing, blocking or destructive (negative) active principle and thereby differ fundamentally from the superagonistic (positive) active principle pursued in the present invention. According to the present invention the selection of the isotypes IgG1 and IgG4 as therapeutic formats of superagonistic anti-CD28 antibodies is based on the following considerations and surprising experimental results: The inventive principle is based on the selection of $F_c$ fragments of the IgG1 or IgG4 isotype. IgG1 antibodies can be efficiently cross-linked by means of $F_c$ receptors present in the body. This should be conducive to the superagonistic active principle (see also Evans et al., Nature Immunol., 2005, 6: 271-279). This was offset, however, by the expectation that such a crosslinking would lead to an elimination of the T cells, which would be contrary to the desired active principle, respectively, it was to be expected that the desired active principle would be undone by this elimination. In the case of the IgG4 isotype it was to be expected in light of the prior art that this isotype would be contrary to the desired activity. For this isotype, for example, an antibody-dependent activity triggering cellular cytotoxicity (ADCC) was described; see Isaacs et al., Clin. Exp. Immunol., 106: 427-433. Moreover, in view of the expected lack of a Fc receptor binding or of very little Fc receptor binding it could not be assumed that this isotype would, for example, promote T cell activation in a culture of peripheral blood leukocytes.

After the binding molecules according to the present invention had been provided, it was surprisingly found that they stimulate T cells superagonistically. This is shown for the antibodies of the IgG1 isotype (TGN1112) and of the IgG4 isotype (TGN1412) in the enclosed examples and in the experimental results depicted in FIGS. 1 to 8. The heavy and the light chain of TGN1412 are depicted in SEQ ID NO: 14 and 16, respectively. SEQ ID NOS: 30 and 32 show the amino acid sequences of the heavy and the light chain of TGN1112. As can be seen from FIGS. 1 to 8, both the light and the heavy chains of the antibodies TGN1112 and TGN1412 are first synthesized with signal peptide (in the Figures referred to as leader peptide). The signal peptide determines the targeting within the cell and is no longer present on the mature light or the mature heavy chain. With regard to the heavy chain of TGN1412 it must also be noted that upon expression in CHO cells two variants of the C terminus were observed, which differ by an additional amino acid residue (FIG. 2). The DNA sequences including introns and UTR and the region encoding the signal peptide are depicted in SEQ ID NOS: 41 and 43 for the heavy and the light chain of TGN1412, respectively, and in SEQ ID NOS: 45 and 47 for the heavy and the light chain of TGN1112, respectively. The amino acid sequences encoded thereby are depicted in SEQ ID NOS: 42, 44, 46 and 48.

In a preferred embodiment, the present invention thus provides the soluble anti-CD28 antibodies TGN1412 and TGN1112 for the polyclonal stimulation of human CD4 and CD8 T lymphocytes in a novel manner independent of TCR. The finding that TGN1412 and TGN1112 in soluble form very efficiently activate and expand the T lymphocytes ex vivo was unexpected. As regards TGN1412, this finding was in particular surprising since on the one hand a crosslinking of the antibody is necessary for the superagonistic active principle, but on the other hand no binding to high-affinity or intermediate-affinity $F_c$ receptors could be detected. As regards TGN1112, this finding was surprising since the antibody in cell culture mediates a strongly pronounced antibody-dependent cytotoxicity vis-à-vis T cells (FIG. 16), but at same time induces a very strong proliferation (FIG. 10A). In comparison with the starting antibody 5.11A1 both TGN1412 and TGN1112 distinguish themselves by being able to keep at a very low level the activation-induced cell death (apoptosis) of human T lymphocytes in cell culture (FIG. 15). This result holds out the prospect that in humans, too, TGN1412 and TGN1112 should be able to activate and expand T lymphocytes extremely efficiently and gently.

The one or more nucleic acid(s) of the present invention preferably comprise(s) a nucleic acid sequence encoding a $V_H$ region and a nucleic acid sequence encoding a $V_L$ region, wherein
(i) the nucleic acid sequence of the VH region comprises SEQ ID NO: 33 or 37 and/or encodes a (poly)peptide comprising the amino acid sequence SEQ ID NO: 34 or 38; and
(ii) the nucleic acid sequence of the VL region comprises SEQ ID NO: 35 or 39 and/or encodes a poly(peptide) comprising the amino acid sequence SEQ ID NO: 36 or 40.

The one or more nucleic acid(s) of the present invention further preferably comprise(s) a nucleic acid sequence
(i) that is SEQ ID NO: 13, 29, 41 or 45; and/or
(ii) encodes a (poly)peptide having the amino acid sequence SEQ ID NO: 14, 30, 42 or 46.

Also preferred are one or more nucleic acid(s) comprising a nucleic acid sequence
(i) that is SEQ ID NO: 15, 31, 43 or 47; and/or
(ii) encodes a (poly)peptide having the amino acid sequence SEQ ID NO: 16, 32, 44 or 48.

Furthermore, it is a preferred object of the invention that one or more nucleic acid(s) according to the present invention additionally comprise(s) a nucleic acid sequence encoding a marker element or tag.

The term "marker element" or "tag" in the context of the present invention describes an element mediating the ability for interaction with a known binding partner. This interaction makes possible uses such as (facilitated) purification or isolation as well as detection or verification.

The marker elements or tags according to the invention may, by way of example, be selected from a group consisting of His-tag, Flag-tag, Myc-tag, HA-tag, GST-tag, T100™, VSV-G, V5, S-tag™, HSV, CFP, RFP, YFP, GFP, BFP, cellulose binding domain (CBD), maltose binding protein (MBP), NusA-tag, thioredoxin (Trx), DsbA, DabC and a biotinylation sequence. Alternatively or in particular, the marker element may be a radioactive, fluorescent, phosphorescent or luminescent marker. Radioactive markers include markers with $^{32}P$ (in case of nucleic acids) and $^{125}I$ or $^{132}I$ (in case of proteins).

An alternative embodiment of the invention relates to a vector comprising one or more of the above described nucleic acids according to the present invention.

The expert molecular biologist knows a large number of suitable vectors. The choice of a vector depends in this connection on the desired properties and includes plasmids, cosmids, viruses, bacteriophages and other vectors conventionally used in genetic engineering. Generally known methods may be used for the preparation of different vectors; see inter alia Sambrook et al., Molecular Cloning: A Laboratory Manual; Cold Spring Harbor Laboratory Press, 2$^{nd}$ edition 1989 and 3$^{rd}$ edition 2001; Gerhardt et al.; Methods for General and Molecular Bacteriology; ASM Press, 1994; Lefkovits; Immunology Methods Manual: The Comprehensive Sourcebook of Techniques; Academic Press, 1997; Golemis; Protein-Protein Interactions: A Molecular Cloning Manual; Cold Spring Harbor Laboratory Press, 2002 and Ausubel, Current Protocols in Molecular Biology, Green Publishing Associates and Wiley Interscience, N.Y. (1989), (1994).

Nucleotide sequences to be expressed can be cloned in suitable expression vectors. Usual cloning vectors comprise pBluescript SK, pGEM, pUC9, pBR322 and pGBT9. Usual expression vectors comprise inter alia pTRE, pCAL-n-EK, pESP-1, pOP13CAT, pKNOH2 and pLNOK (Norderhaug et al., 1997, J. Immunol. Methods, 204: 77-87).

A vector according to the present invention usually comprises a "regulatory sequence" operatively linked with the nucleotide sequences to be expressed. The term "regulatory sequence" describes DNA sequences necessary for initiating the expression of an encoded sequence. The properties of such control sequences differ depending on the host organism.

The term "operatively linked" describes an arrangement in which the mentioned components are arranged in a manner suitable for expression. The suitable arrangement is known to the skilled person.

Preferably, the vector described is an expression vector. An expression vector is a construct that is suitable for transforming a selected host and allows the expression of the encoded sequence in the host. Accordingly, expression vectors may be cloning vectors, binary vectors or integrated vectors. Expression comprises the transcription of the nucleic acid, preferably in translatable mRNA. Regulatory elements ensuring an expression in prokaryotes and/or eukaryotic cells are known to the skilled person. Control sequences for prokaryotes generally comprise a promoter, a ribosomal binding site and a terminator. Possible regulatory elements for prokaryotic hosts comprise for example PL, lac, trp or tac promoters from *E. coli*. Control sequences for eukaryotic cells comprise in general promoters and terminators and possibly enhancers, transactivators or transcription-factor binding sites. Promoters ensure initiation of the transcription. Terminators, such as poly-A signals, ensure termination of the transcription and stabilization of the transcript. Examples of regulatory elements for eukaryotic host cells are, for example, the AOX1 or GAL1 promoter for yeasts or the CMV, the SV40, the RSV promoter (Rous Sarcoma virus), the CMV enhancer, SV40 enhancer or a globin-intron for mammal cells or other animal cells. Expression vectors known in this context from the prior art comprise, inter alia, vectors, such as the Okayama-Berg cDNA expression vector pcDV1 (Pharmacia), pCDM8, pRc/CMV, pcDNAI, pcDNA3 (InVitrogen), pEF-DHFR and pEF-ADA (Raum et al., Cancer Immunol. Immunother (2001) 50(3), 141-150), pSPORT1 (GIBCO BRL), as well as pKNOH2 and pLNOK (Norderhaug et al., 1997, J. Immunol. Methods, 204: 77-87).

The term "control sequence" is used to describe all sequences necessary for at least one expression in a selected host and thus may comprise further components.

The present invention further relates to a host that is transformed or transfected with a vector as described above.

This host may be a prokaryote or preferably a eukaryotic cell.

Prokaryotic hosts in the context of the present invention comprise all eubacteriae and archaebacteriae that can be transformed by the nucleic acids. Thus, this group comprises gram-negative and gram-positive bacteria, such as *E. coli, S. typhimurium, Serratia marcescens* and *Bacillus subtilis*. Eukaryotic cells comprise inter alia yeasts, higher plants, insects, and, preferably, mammal cells, such as CHO, COS-7, NSO and Per.C6 cells.

The invention further relates to a method for preparing a binding molecule encoded by one or more of the above described nucleic acids, comprising culturing the host of the invention under suitable conditions, and isolating the binding molecule from the culture.

The transformed/transfected host can be cultured in a fermentor. Protocols for the growth/cultivation of different hosts are known to the skilled person. They can be determined and optimized without further inventive activity. Also, the skilled person is familiar with methods for the isolation of a recombinant (poly)peptide as well as of the binding molecule according to the present invention from a culture or a culture supernatant. Such isolation methods comprise inter alia ammonium sulfate precipitation, affinity purifications (e.g. by means of chromatography columns), gel electrophoresis and the like; see, inter alia, Scopes, "Protein Purification", Springer-Verlag, N.Y. (1982) or Rehm, "Der Experimentator: Proteinbiochemie/Proteomics", Spektrum, Akademischer Verlag. Essentially pure preparations of binding molecules with a homogeneity of 90 to 95%, preferably of 98 to 99% or with an even higher homogeneity are preferred for pharmaceutical applications.

In a further embodiment, the invention relates to a binding molecule encoded by one or more nucleic acid(s) according to the present invention or prepared according to the method of the invention.

Antibodies or fragments or derivatives of an antibody which correspond to or contain a binding molecule according to the present invention are preferred. Antibody fragments in the sense of the invention comprise fragments of the above described antibodies that comprise the specific binding properties of the defined variable regions and also possess a part of the constant region of an IgG1 or IgG4 antibody enabling crosslinking.

Derivatives of antibodies according to the present invention comprise, but are not limited to, marked antibodies/antibody fragments, as well as chemically modified antibodies/antibody fragments. The antibodies/antibody fragments can be marked/modified posttranslationally or by chemical/biochemical or molecular biological modification. These modifications comprise for example a modification of the glycosylation (Umana et al., 1999, Nature Biotech. 17: 176-180) and a PEGylation (Delgado et al., 1996, J. Drug Target. 3: 321-340).

The antibody according to the present invention is preferably a monoclonal antibody.

In an alternative embodiment, the present invention relates to a composition comprising the nucleic acid(s) according to the present invention, a vector according to the present invention, a host, binding molecule and/or the antibody or fragment or derivative of an antibody.

Preferably the composition of the invention is a pharmaceutical composition. Optionally, it may further comprise a pharmaceutically acceptable carrier, a pharmaceutically acceptable excipient or a pharmaceutically acceptable diluent.

A pharmaceutical composition according to the present invention comprises inter alia Pharmaceuticals and pharmaceutical preparations. Examples of particularly suitable pharmaceutically/pharmacologically acceptable carriers/excipients and diluents are known to the skilled person. They comprise buffered saline, water, emulsions, such as oil/water emulsions, different types of detergents, sterile solutions, etc. Pharmaceuticals comprising such carriers can be formulated by known conventional methods. The pharmaceutical composition according to the present invention can be administered to an individual in a suitable dose. It can be administered parenterally, e.g. intravenously, intraperitoneally, subcutaneously, intramuscularly, topically, intranasally, intrabronchially or intradermally, or via a catheter at one place in an artery. The kind of dosage is determined by the attending physician corresponding to the clinical factors. It is known to the skilled person that the kind of dosage depends on various factors, such as body height and weight, body surface, age, sex or general health of the patient, but also on the specific preparation to be administered, the duration and kind of administration, and of other medicaments possibly administered in parallel. A typical dose may, for example, lie in a range between 0.001 and 500,000 µg, whereby doses below or above this exemplary range, especially taking into account the above mentioned factors, are conceivable, too. In general, if the composition of the invention is regularly administered, the dose should be in a range between 10 ng and 10 mg units per day or per application interval. When the composition is administered intravenously, the dose should be in a range between 1 ng and 1 mg units per kilogram bodyweight per minute.

The pharmaceutical composition according to the present invention can be administered topically or systemically. Preparations for parenteral administration comprise sterile aqueous or non-aqueous solutions, suspensions and emulsions. Examples for non-aqueous solvents are propylene glycol, polyethylene glycol, vegetable oils, such as olive oil, and organic ester compounds, such as ethyloleate, suitable for injections. Aqueous carriers comprise water, alcohol-water solutions, emulsions, suspensions, salt solutions and buffered media. Parenteral carriers comprise sodium chloride solutions, Ringer dextrose, dextrose and sodium chloride, Ringer lactate and bound oils. Intravenous carriers comprise e.g. fluid, nutrient and electrolyte supplements (e.g. such as are based on Ringer dextrose). The composition according to the present invention may also comprise preservatives and other additions, such as antimicrobial compounds, antioxidants, complexing agents and inert gases, and/or substances enhancing solubility, such as Tween. Furthermore, depending on the intended use, compounds may be contained such as interleukins, growth factors, differentiation factors, interferons, chemotactic proteins or an unspecific immunomodulatory agent.

Alternatively, it is preferred that the composition according to the present invention is a diagnostic composition.

Preferably, the composition according to the present invention is a kit comprising the nucleic acid(s), the vector, the host, the binding molecule, and/or the antibody or fragment or derivative of an antibody in one or more containers. More preferably, this kit also comprises a package insert (instruction leaflet) which may contain a description of the kit, of its components and/or its use. The description of the use may, moreover, also comprise dosage information for physicians.

In one embodiment, the invention relates to the use of the nucleic acid(s) according to the present invention, the vector according to the present invention, the host according to the present invention, the binding molecule according to the present invention and/or the antibodies according to the present invention or fragments or derivatives of an antibody according to the present invention for the preparation of a pharmaceutical composition for the treatment of diseases associated with a faulty or deficient co-stimulability, function or number of T cells, of inflammatory diseases and/or autoimmune diseases.

Alternatively, the invention relates to a method for the treatment of diseases associated with faulty co-stimulability, defective function or a deficient number of T cells, of inflammatory diseases, and/or autoimmune diseases, comprising the administration of the nucleic acid(s) according to the present invention, the vector according to the present invention, the host according to the present invention, the binding molecule according to the present invention, and/or of the antibody according to the present invention or of fragments or derivatives of an antibody according to the present invention.

Uses and methods according to the present invention are preferred when the diseases associated with faulty co-stimulability, function or number of T cells, are selected from the group consisting of chronic lymphocytic leukemia of the B cell type (B-CLL), acute lymphoblastic leukemia (ALL), T lymphopenia, solid tumors, HIV infection and HTLV infection. The solid tumors are preferably selected from renal carcinoma, pulmonary carcinoma and melanomas.

Alternatively preferred are uses and methods wherein the inflammatory and autoimmune diseases are selected from the group consisting of rheumatoid arthritis (RA), Diabetes mellitus type I, multiple sclerosis, psoriasis, Guillain-Barre syndrome, Crohn's Disease, and diseases ascribed to undesirable T cell activation reactions, such as "graft-versus-host disease" (GvHD) or "host-versus-graft disease" (HvGD). The HvGDs especially focus on the rejection of solid organ transplants, such as liver, lung, heart and kidneys.

In a further alternative embodiment, the invention relates to the use of the nucleic acid(s) according to the present invention, the vector according to the present invention, the host according to the present invention, the binding molecule according to the present invention and/or of the antibody according to the present invention or of the fragment or derivative of an antibody for the preparation of a diagnostic composition for in-vitro analysis of a patient's responsiveness to a therapy with a pharmaceutical composition.

An in-vitro analysis that can be carried out with this diagnostic composition comprises, for example, the following steps:
(a) isolation of blood cells from a blood sample (e.g. PBMCs (peripheral blood mononuclear cells) and/or lymphocytes);
(b) incubation of the blood cells with an antibody according to the present invention and optionally addition of an exogenous crosslinking reagent;
(c) detection of an antibody-dependent stimulation of T cells in the sample.

When an antibody-dependent stimulation of T cells is detected in the sample, the patient from whom the sample has been taken is responsive to a therapy with a pharmaceutical composition according to the present invention.

BRIEF DESCRIPTION OF THE DRAWINGS

FIGS. 1-8: show the nucleotide and amino acid sequences of the light and heavy chains of TGN1412 and TGN1112.

Figure 9:
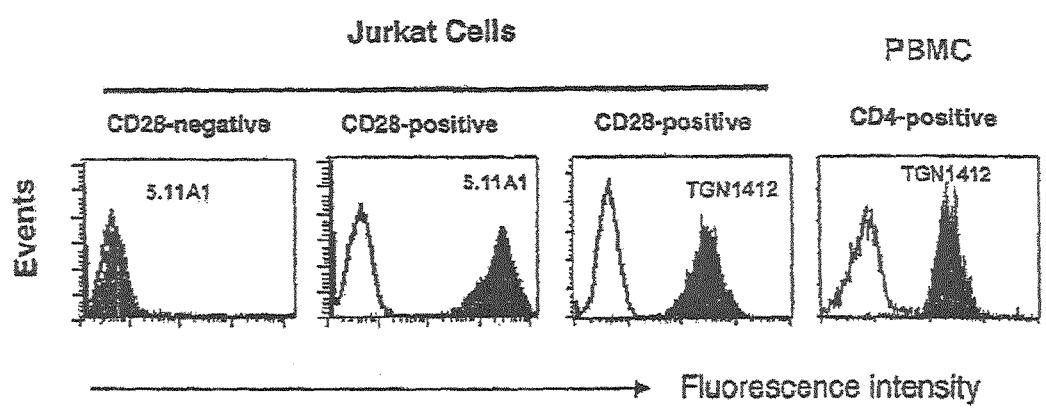
FIG. 9: Binding specificity of the antibodies TGN1412 and 5.11A1 for CD28 on transfected Jurkat cells and on primary human T cells. For immune fluorescence staining and flow cytometry, 1-2×10$^6$ cells/ml in FACS buffer (PBS, BASA, Na acid) each were incubated for 40 minutes at 4° C. with saturating amounts of the antibodies 5.11A1, TGN1412-irrelevant isotype-specific control antibodies. Each staining was washed to remove excess antibodies and, prior to analysis, incubated for 15 minutes with saturating amounts of PE-conjugated anti-mouse IgG (for 5.11A1) or PE-conjugated anti-human IgG (for TGN1412). Subsequently, the cells were counterstained with anti-CD4 antibodies. The flow cytometric analysis was carried out on a FACSCalibur™ by means of the Cell Quest™ software (Becton Dickinson). Fluorescence signals and side scatter signals (ssc) were recorded logarithmically, forward scatter signals (fsc) linearly. Histograms consistently show signals of cells lying in an empirical "life gate", defined by ssc and fsc. They show the binding of 5.11A1 or TGN1412 (filled-in curves) compared to isotype-control antibodies (open curves) on Jurkat cells which do not express CD28 (left-hand diagram) or were transfected with CD28 (central diagrams) as well as on CD4-positive peripheral blood mononuclear cells (PBMC), right-hand diagram).

(A) PBMC (collection and culture conditions see FIG. 10) were stimulated for the periods indicated with TGN1412 (1 µg/ml) or an isotype-control antibody. The cell cyclus status for CD4 and CD8 cells was determined by intracellular staining by means of FITC-labelled anti-Ki67 antibodies. For this purpose, cells were incubated with anti-human CD4 PE or anti-CD8 PE antibodies for 15 minutes, washed and incubated in Cytofix/Cytoperm™ buffer (Becton Dickinson) for 20 minutes at 4° C. After washing with PermAA/ash™ buffer (Becton Dickinson) the cells were stained for further 30 minutes at 4° C. with anti-Ki-67-FITC, washed and measured by flow cytometry as described under FIG. 9.

(B) CD4+ or CD8+ T cells were collected from a PBMC suspension by means of suitable T cell isolation kits and subsequent AutoMACS™ separation (both from Miltenyi). The purity analyzed by flow cytometric analysis was 93-98% for CD4+ and 81-95% for CD8+ T cells. 96-well flat bottom plates were coated with anti-human Ig (40 µg/ml in PBS) for 3 h at room temperature and subsequently washed. The cells were then cultured in a density of $1 \times 10^5$/well together with TGN1412 or a reference antibody. The addition of PHA (5 µg/ml) and IL-2 (200 U/ml) served as positive control for cell proliferation. The proliferation was determined after 48 hours as described for FIG. 10 and represents a representative result for various donors.

Figure 13:
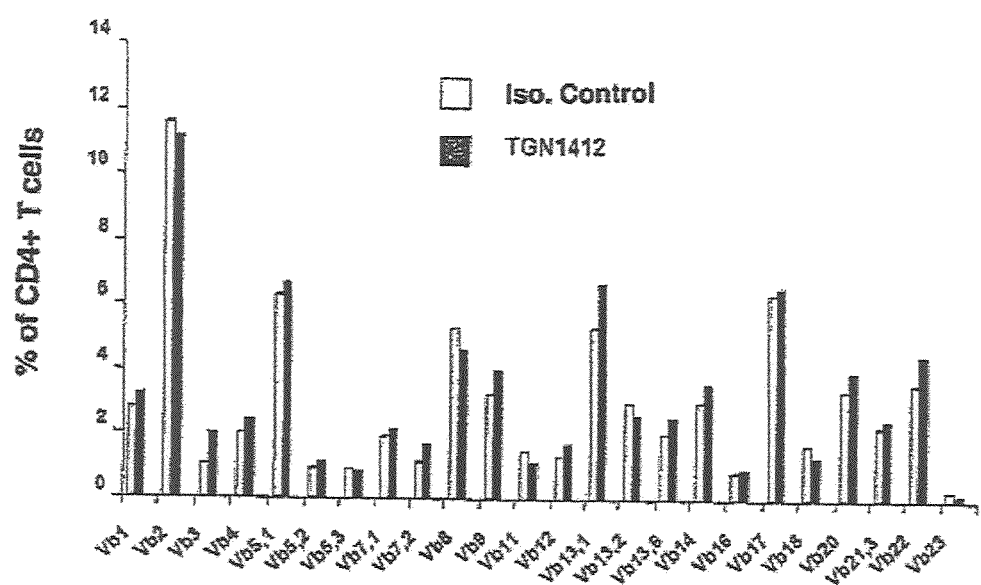

FIG. 13: Analysis of the TCR repertoire of PBMC stimulated by TGN1412. The TCR V[beta] repertoire analysis of PBMC cultivated for 96 hours with TGN1412 (1 µg/ml) or an IgG4 control antibody was carried out by means of the IOTest® Beta Mark TCR V[beta] Repertoire Kit™ (Beckman Coulter) according to the manufacturer's instructions. Samples were counterstained with anti-CD3 and anti-CD4 antibodies as described for FIG. 9. What is depicted is a representative result of three measurements wherein the analysis window was set to CD3+ CD4+ cells.

Figure 14:
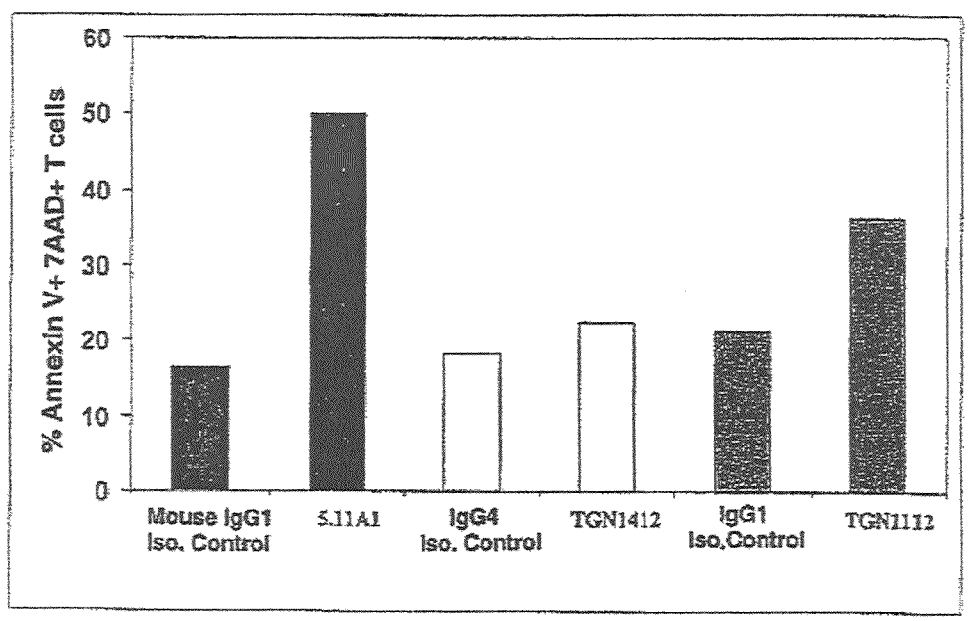

FIG. 14: Measurement of the T cell apoptosis mediated by anti-CD28. PBMC ($2 \times 10^5$/ml) were incubated for 72 hours with soluble 5.11A1, TGN1412, TGN1112 or isotype control antibody (1 µg/ml). Subsequently, the cells were stained for 15 minutes with anti-CD3-APC and washed with FACS buffer. PMBC were resuspended in Annexin V Binding Buffer (BD Pharmingen) and incubated for 15 minutes with anti-Annexin V and 7AAD. The apoptosis in the sense of T cells (CD3+ window) that were Annexin V-positive and 7AAD-permeable was determined within 1 hour by means of flow cytometry.

Figure 15:
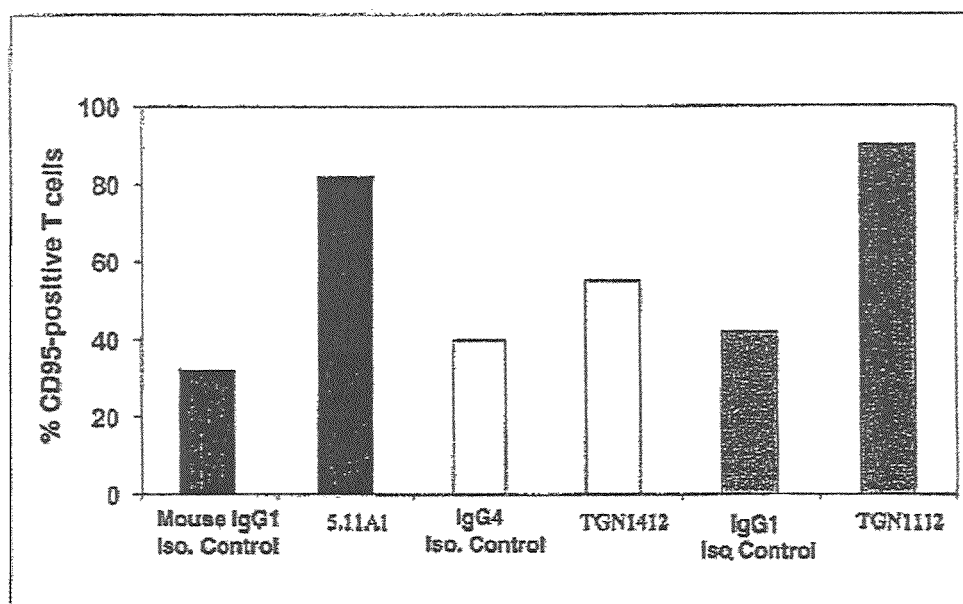

FIG. 15: Induction of the pro-apoptic receptor CD95 by anti-CD28 antibodies. The experimental setup corresponds to the one described in FIG. 14. Instead of Annexin V/7AAD staining, PBMC were stained with anti-CD3 FITC and CD95-PE and the expression of CD95 was determined on CD3+ T cells by means of flow cytometry. What is shown is an exemplary result for two different donors.

Figure 16:
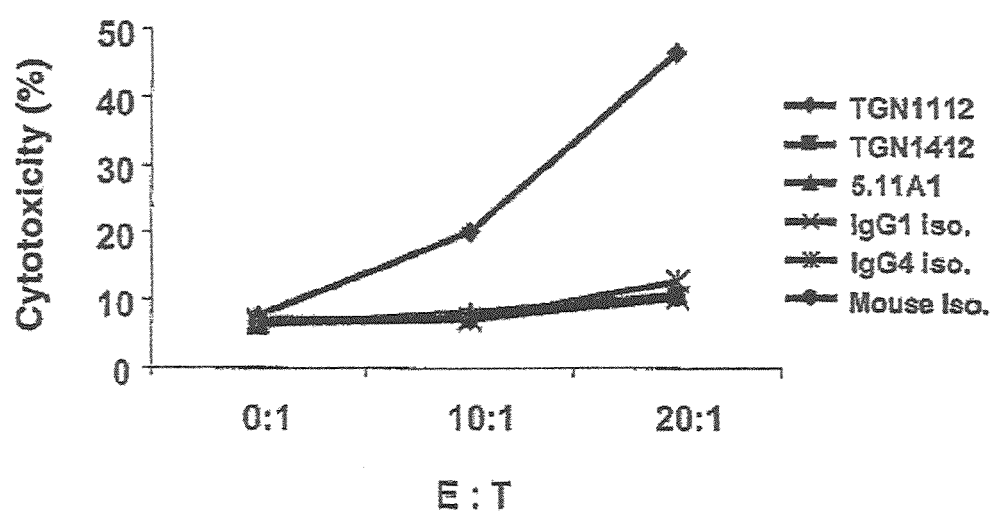

FIG. 16: Induction of antibody-dependent cellular cytotoxicity, ADCC. The ADCC of diverse anti-CD28 antibodies was determined by flow cytometry. For this purpose, $5 \times 10^4$ Calcein-AM labelled CD28+ Jurkat cells were co-cultured for 3.5 hours with newly isolated PBMC in the presence of 6 µg/ml of the indicated antibodies in the shown effector to target cell ratios (E:T). The cells were received in FACS buffer with 0.5 µg/ml propidium-iodide and measured by flow cytometry. The ratio of Calcein-negative or Calcein-weakly positive cells/propidium iodide-positive cells (×100) to complete Calcein-positive cells was determined as percentage of cytotoxicity. What is shown is a representative result of determinations with cells from different donors.

FIG. 17: CDRs of the binding molecules according to the present invention according to the Kabat system and according to the AbM/Kabat combi system.

The examples illustrate the invention. The examples must not be construed as restricting the invention. The examples merely serve to illustrate the invention which is only restricted by the claims.

EXAMPLE 1

Binding Properties of the Antibodies According to the Present Invention to CD28, CD16B, CD32 and CD64

It was investigated whether during the humanization process the binding to the human CD28 molecule was retained. As exemplarily shown in FIG. 9 for TGN1412, this was the case for both isotypes.

Subsequently, the binding properties of TGN1412 and TGN1112 to CD16b, CD32 and CD64 were determined. The results are compiled in Table 1. As expected, it was found that TGN1112 bound with easily detectable affinity to CD16 and CD64, but not to CD32, while TGN1412 interacted only weakly and exclusively with CD64.

TABLE 1

Binding properties of TGN1412 and TGN1112 to human Fc gamma receptors

| FcγR | TGN1112 | TGN1412 |
|---|---|---|
| CD16b | + | − |
| CD32 | − | − |
| CD64 | ++ | + |

Legend:
− not detectable
+ average binding
++ strong binding

Table 1: The binding of TGN1412 and TGN1112 to FcγRIIIb (CD16b) was measured by means of ELISA, with human recombinant CD16b (R&D Systems) serving as "capture antigen". The interaction between CD16b and TGN1112 was shown by means of HRP-conjugated anti-human light chain kappa Ig. To verify the binding of TGN1112 or TGN1412 to CD32 and CD64, human CD28-negative cell lines constitutively expressing CD32 and/or CD64, were incubated for 40 minutes with TGN1112 or TGN1412, washed and counterstained with a PE-conjugated anti-human IgG antibody recognizing the kappa chain. Cells were washed and the binding of TGN1112 and TGN1412 to FcγR was detected by means of flow cytometry. The specificity for CD64 was determined on cell lines expressing both CD32 and CD64, by competition experiments with blocking anti-CD64 antibody.

EXAMPLE 2

T Cell Stimulation by the Antibodies According to the Present Invention

In the following, experimental findings are explained showing that surprisingly both TGN1112 and TGN1412 are able to activate ex-vivo human T lymphocytes without artificial crosslinking. In view of the fact that TGN1412 only weakly binds to the Fc receptor CD64, this could, in particular, not be expected for TGN1412.

Figure 10:
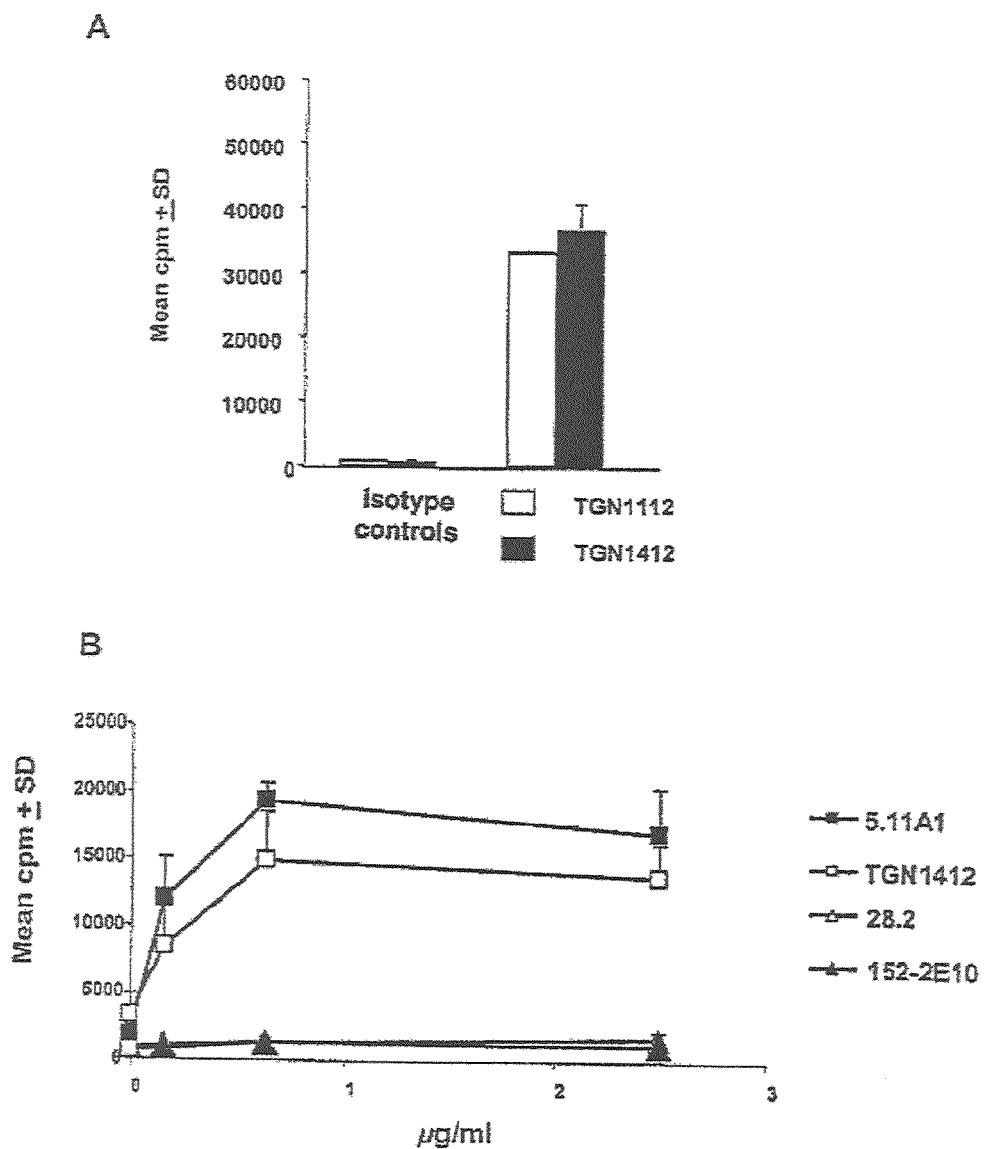
FIGS. 10A and 10B: Cell collection and proliferation tests. PBMC were isolated from newly obtained peripheral blood or from Buffy Coats by Ficoll density centrifugation, washed and brought to culture in a concentration of $2 \times 10^5$ cells per 200 µl well in round-bottom 96-well plates. In accordance with the labelling they were cultured with soluble TGN1112, TGN1412, 5.11A1 or isotype-control antibodies in a concentration of 1 µg/ml (A) or corresponding to the labelling on the abscissa (B). After 48 hours, the relative cell proliferation rate was—shown as mean cpm±SD=mean value, counts per minute±standard deviation—determined by means of [methyl-$^3$H] thymidine integration over a period of 18 hours and subsequent liquid scintillation measurement. The results are representative for multiple determinations with diverse donors.

It was first investigated whether the T-cell-activating properties of the humanized antibodies were retained vis-a-vis the basic antibody 5.11A1. The surprising result is shown in FIG. 10 by way of example. In FIG. 10A it is shown that both TGN1112 and TGN1412 in soluble form are able to efficiently stimulate peripheral blood mononuclear cells (PBMC) to proliferate in cell suspension. In FIG. 10B it is shown that the induction of the proliferation of T cells by TGN1412 was equally strong as the induction of the proliferation by the basic antibody 5.11A1, but that conventional, i.e., non-superagonistic anti-CD28 antibodies, such as the antibodies 28.2 or 152-2E10, are not able to induce proliferation.

EXAMPLE 3

Relevance of the Fc Domain for the Stimulatory Properties

Figure 11:
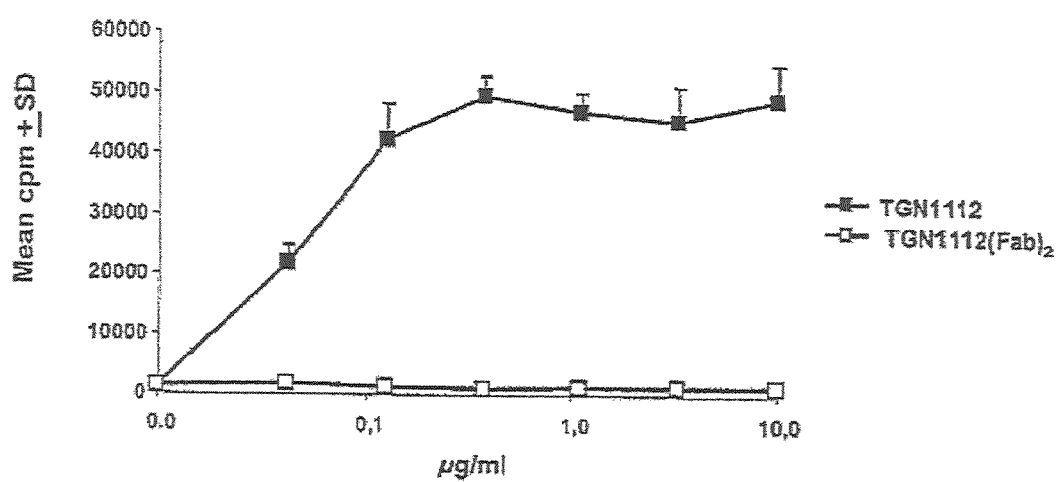
FIG. 11: Cell collection, PBMC stimulation and presentation were as described for FIG. 10. The stimulation of TGN1112 was compared with that of TGN1112(Fab)$_2$ fragments, biochemical quality and specific binding of which to CD28 transfectants had previously been shown.

It was then investigated whether the $F_c$ domain is necessary for the stimulatory properties vis-à-vis human T cells in a culture of PBMC. For this purpose, fragments of TGN1112F (ab)$_2$ were prepared and compared with intact antibodies in cell culture regarding the activation of PBMC. The result is shown in FIG. 11. It was found that F(ab)$_2$ fragments of TGN1112 induced no proliferation whatsoever, whereas the intact antibodies, depending on their dosage, induced a strong proliferation of PBMC.

EXAMPLE 4

Figure 12:
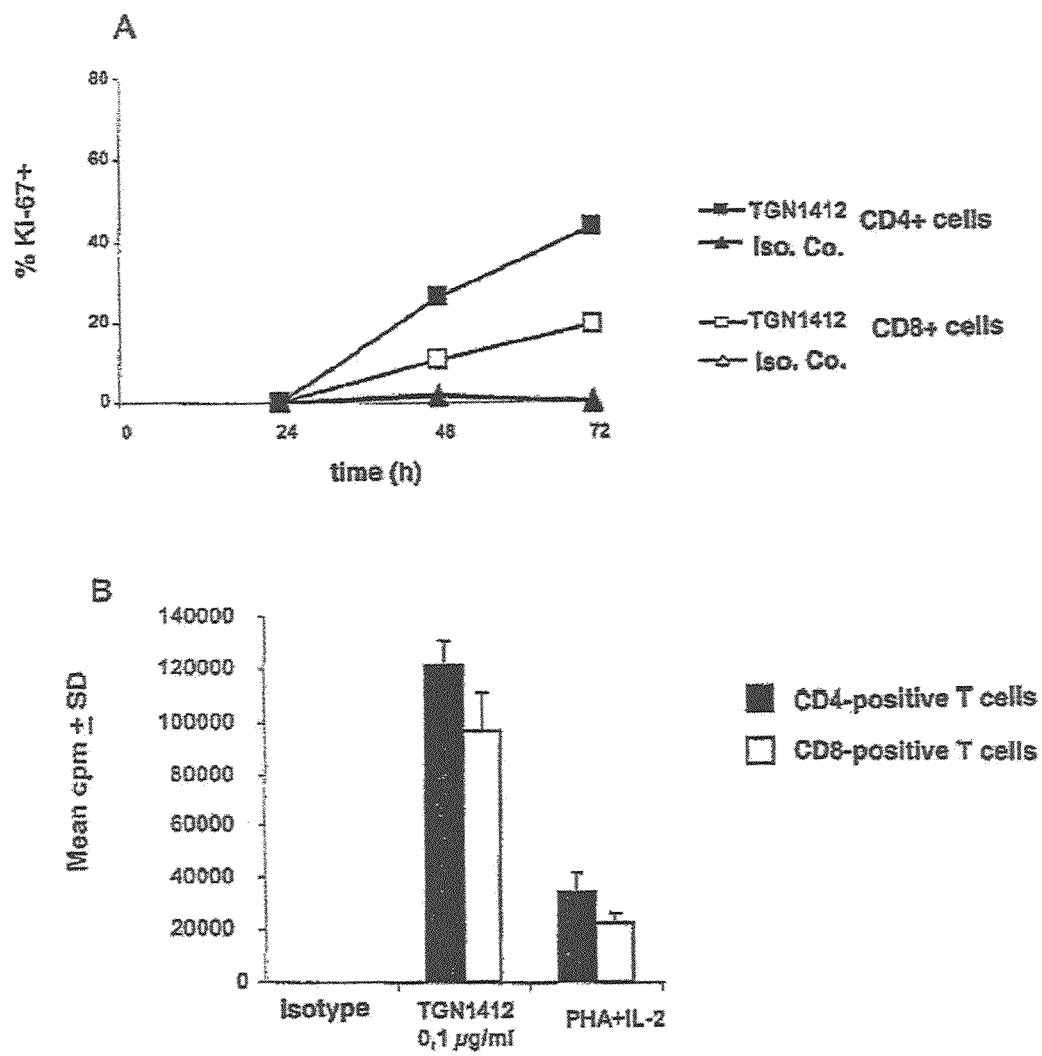
FIGS. 12A and 12B: Stimulation of CD4 and CD8 T cells by TGN1412.

T Cells are the Target Cells of the Stimulatory Activity of the Antibodies According to the Present Invention To show that the cells in the PBMC culture proliferating by TGN1412 stimulation were T cells, the analysis of the cell cycle marker Ki-67 was combined with the analysis of the surface markers CD4 and CD8. The expression of CD4 and CD8 characterizes the two main groups of T cells, T helper cells (expressing CD4) and cytotoxic T cells (expressing CD8). In FIG. 12A it is shown that soluble TGN1412 in a PBMC suspension clearly incites the proliferation of both subgroups. In FIG. 12B it is shown that also purified CD4 and CD8 T lymphocytes are clearly induced by TGN1412 stimulation to proliferate, however, in this system the presence of a crosslinking agent is required.

In FIG. 13 it is shown that by the TGN1412-mediated expansion of CD4 T cells in cell culture the repertoire of the TCRVB expression is retained. This is an important finding to the effect that in the desired immune therapy it is advantageous to preserve the naturally occurring variety of the TCR repertoire in order to obtain immune tolerance and to ensure reactivity vis-à-vis a broad spectrum of possible causative agents.

In summary, these findings surprisingly show that both TGN1412 and TGN1112 in soluble form are able to stimulate human T cells in cell culture.

EXAMPLE 5

High Stimulatory and Low Pro-Apoptotic Effects of the Antibodies According to the Present Invention Subsequently, the T cell activation mediated by TGN1412, TGN1112 and the basic antibody 5.11A1 was investigated in more detail with regard to the induction of programmed cell death (apoptosis). Representative results are summarized in FIGS. 14 and 15.

FIG. 14 shows that the proportion of apoptotic T cells in a PBMC culture stimulated with the anti-CD28 antibodies 5.11A1, TGN1412 and TGN1112 in soluble form, was most pronounced in the 5.11A1-stimulated cultures, intermediately pronounced in the TGN1112-stimulated cultures, and least pronounced in the TGN1412-stimulated cultures. In accordance with these results, FIG. 15 shows that the apoptosis-triggering receptor CD95 was most often expressed on T cells stimulated with 5.11A1, while TGN1112-stimulated cells showed an intermediate and TGN1412-stimulated T cells a low frequency of CD95-positive cells.

LITERATURE

Delgado et al., 1996, J. Drug Target. 3: 321-340

Evans et al., Nature Immunol., 2005, 6: 271-279

Ewert et al., 2004, Methods, 34: 184-199

Hwang et al., Methods, 2005, 36: 3-10

Isaacs et al., Clin. Exp. Immunol., 106: 427-433

Johnson, G. and Wu, T. T., 2000, Nucleic Acids Research

Jones et al., 1986, Nature 321: 522-525

Kabat, E. A. et al. 1991; Sequences of Proteins of Immunological Interest, Fifth Edition. NIH Publication No. 91-3242

Lin et al., Eur. J. Immunol., 2003, 33:626-638

Luhder et al., J. Exp. Med., 2003, 197: 955-966

Norderhaug et al., 1997, J. Immunol. Methods, 204: 77-87

Schmidt et al., J. Neuroimmunol., 2003, 140: 143-152

Schwartz, Nature Immunol., 2005, 6: 327-330

Tacke et al., Eur. J. Immunol., 1997, 27:239-247

Umana et al., 1999, Nature Biotech. 17: 176-180

Woof et al., Nature Reviews Immunol., 2004, 1-11

What is claimed is:

1. A pharmaceutical composition comprising a binding molecule that specifically binds a human CD28 molecule, wherein the binding molecule is encoded by a nucleic acid sequence comprising:
   (a) a nucleic acid sequence encoding a $V_H$ region and a nucleic acid sequence encoding a $V_L$ region comprising CDRs in a human immunoglobulin framework, wherein
      (i) the CDRs of the VH region (CDR-H) comprise the amino acid sequences of SEQ ID NOS: 2 or 18 (CDR-H3), 4 or 20 (CDR-H2) and 6 or 22 (CDR-H1) or are encoded by the nucleic acid sequences of SEQ ID NOS: 1 or 17 (CDR-H3), 3 or 19 (CDR-H2) and 5 or 21 (CDR-H1); and
      (ii) the CDRs of the VL region (CDR-L) comprise the amino acid sequences of SEQ ID NOS: 8 or 24 (CDR-L3), 10 or 26 (CDR-L2) and 12 or 28(CDR-L1) or are encoded by the nucleic acid sequences of SEQ ID NOS: 7 or 23 (CDR-L3), 9 or 25 (CDR-L2) and 11 or 27 (CDR-L1); and
   (b) a nucleic acid sequence encoding the constant region of a human IgG1 or IgG4 antibody;
and a pharmaceutically acceptable molecule.

2. The composition of claim 1, wherein
   (i) the nucleic acid sequence encoding the VH region comprises SEQ ID NO: 33 or 37 and/or encodes a (poly)peptide comprising the amino acid sequence SEQ ID NO: 34 or 38; and
   (ii) the nucleic acid sequence encoding the VL region comprises SEQ ID NO: 35 or 39 and/or encodes a (poly)peptide comprising the amino acid sequence SEQ ID NO: 36 or 40.

3. The composition of claim 1, wherein the nucleic acid sequence
   (i) is selected from the group consisting of SEQ ID NO: 13, 29, 41 and 45; and/or
   (ii) encodes a (poly)peptide having an amino acid sequence selected from the group consisting of SEQ ID NO: 14, 30, 42 and 46.

4. The composition of claim 1, wherein the nucleic acid sequence
   (i) is selected from the group consisting of SEQ ID NO: 15, 31, 43 and 47; and/or
   (ii) encodes a (poly)peptide having an amino acid sequence selected from the group consisting of SEQ ID NO: 16, 32, 44 and 48.

5. The composition of claim 1, wherein the composition further comprises at least one pharmaceutically acceptable molecule selected from the group consisting of: a pharmaceutically acceptable carrier, a pharmaceutically acceptable excipient, and a pharmaceutically acceptable diluent.

* * * * *

SEQUENCE LISTING

<160> NUMBER OF SEQ ID NOS: 48

<210> SEQ ID NO 1
<211> LENGTH: 33
<212> TYPE: DNA
<213> ORGANISM: Artificial sequence
<220> FEATURE:
<223> OTHER INFORMATION: Synthetic construct

<400> SEQUENCE: 1
tcacactacg gcctcgactg gaacttcgat gtc                33

<210> SEQ ID NO 2
<211> LENGTH: 11
<212> TYPE: PRT
<213> ORGANISM: Artificial sequence
<220> FEATURE:
<223> OTHER INFORMATION: Synthetic construct

<400> SEQUENCE: 2

Ser His Tyr Gly Leu Asp Trp Asn Phe Asp Val
1               5                   10

<210> SEQ ID NO 3
<211> LENGTH: 51
<212> TYPE: DNA
<213> ORGANISM: Artificial sequence
<220> FEATURE:
<223> OTHER INFORMATION: Synthetic construct

<400> SEQUENCE: 3
tgtatttatc ctggaaatgt caatactaac tataatgaga agttcaagga c        51

<210> SEQ ID NO 4
<211> LENGTH: 17
<212> TYPE: PRT
<213> ORGANISM: Artificial sequence
<220> FEATURE:
<223> OTHER INFORMATION: Synthetic construct

<400> SEQUENCE: 4

Cys Ile Tyr Pro Gly Asn Val Asn Thr Asn Tyr Asn Glu Lys Phe Lys
1               5                   10                  15

Asp

<210> SEQ ID NO 5
<211> LENGTH: 30
<212> TYPE: DNA
<213> ORGANISM: Artificial sequence
<220> FEATURE:
<223> OTHER INFORMATION: Synthetic construct

<400> SEQUENCE: 5
ggatacacct tcaccagcta ctatatacac                30

<210> SEQ ID NO 6
<211> LENGTH: 10
<212> TYPE: PRT
<213> ORGANISM: Artificial sequence
<220> FEATURE:
<223> OTHER INFORMATION: Synthetic construct

<400> SEQUENCE: 6

Gly Tyr Thr Phe Thr Ser Tyr Tyr Ile His
1               5                   10

-continued

```
<210> SEQ ID NO 7
<211> LENGTH: 27
<212> TYPE: DNA
<213> ORGANISM: Artificial sequence
<220> FEATURE:
<223> OTHER INFORMATION: Synthetic construct

<400> SEQUENCE: 7
caacagggtc aaacttatcc gtacacg                                          27

<210> SEQ ID NO 8
<211> LENGTH: 9
<212> TYPE: PRT
<213> ORGANISM: Artificial sequence
<220> FEATURE:
<223> OTHER INFORMATION: Synthetic construct

<400> SEQUENCE: 8

Gln Gln Gly Gln Thr Tyr Pro Tyr Thr
1               5

<210> SEQ ID NO 9
<211> LENGTH: 21
<212> TYPE: DNA
<213> ORGANISM: Artificial sequence
<220> FEATURE:
<223> OTHER INFORMATION: Synthetic construct

<400> SEQUENCE: 9
aaggcttcca acctgcacac a                                                21

<210> SEQ ID NO 10
<211> LENGTH: 7
<212> TYPE: PRT
<213> ORGANISM: Artificial sequence
<220> FEATURE:
<223> OTHER INFORMATION: Synthetic construct

<400> SEQUENCE: 10

Lys Ala Ser Asn Leu His Thr
1               5

<210> SEQ ID NO 11
<211> LENGTH: 33
<212> TYPE: DNA
<213> ORGANISM: Artificial sequence
<220> FEATURE:
<223> OTHER INFORMATION: Synthetic construct

<400> SEQUENCE: 11
catgccagtc aaaacattta tgtttggtta aac                                   33

<210> SEQ ID NO 12
<211> LENGTH: 11
<212> TYPE: PRT
<213> ORGANISM: Artificial sequence
<220> FEATURE:
<223> OTHER INFORMATION: Synthetic construct

<400> SEQUENCE: 12

His Ala Ser Gln Asn Ile Tyr Val Trp Leu Asn
1               5                   10

<210> SEQ ID NO 13
<211> LENGTH: 2178
<212> TYPE: DNA
```

<213> ORGANISM: Artificial sequence
<220> FEATURE:
<223> OTHER INFORMATION: Synthetic construct

<400> SEQUENCE: 13

| | | | | | |
|---|---|---|---|---|---|
| caggtgcagc | tggtgcagtc | tggggctgag | gtgaagaagc | ctggggcctc | agtgaaggtc | 60 |
| tcctgcaagg | cttctggata | caccttcacc | agctactata | tacactgggt | gcgacaggcc | 120 |
| cctggacaag | ggcttgagtg | gattggatgt | atttatcctg | gaaatgtcaa | tactaactat | 180 |
| aatgagaagt | tcaaggacag | ggccaccctg | accgtagaca | cgtccatcag | cacagcctac | 240 |
| atggagctga | gcaggctgag | atctgacgac | acggccgtgt | atttctgtac | aagatcacac | 300 |
| tacggcctcg | actggaactt | cgatgtctgg | ggccaaggga | ccacggtcac | cgtctcctca | 360 |
| ggtgagtcgt | acgctagcaa | gctttctggg | gcaggccggg | cctgactttg | gctgggggca | 420 |
| gggaggggc | taaggtgacg | caggtggcgc | cagccaggtg | cacacccaat | gcccatgagc | 480 |
| ccagacactg | gaccctgcat | ggaccatcgc | ggatagacaa | gaaccgaggg | gcctctgcgc | 540 |
| cctgggccca | gctctgtccc | acaccgcggt | cacatggcac | cacctctctt | gcagcttcca | 600 |
| ccaagggccc | atccgtcttc | ccctggcgc | cctgctccag | gagcacctcc | gagagcacag | 660 |
| ccgccctggg | ctgcctggtc | aaggactact | tccccgaacc | ggtgacggtg | tcgtggaact | 720 |
| caggcgccct | gaccagcggc | gtgcacacct | tcccggctgt | cctacagtcc | tcaggactct | 780 |
| actccctcag | cagcgtggtg | accgtgccct | ccagcagctt | gggcacgaag | acctacacct | 840 |
| gcaacgtaga | tcacaagccc | agcaacacca | aggtggacaa | gagagttggt | gagaggccag | 900 |
| cacagggagg | gagggtgtct | gctggaagcc | aggctcagcc | ctcctgcctg | gacgcaccc | 960 |
| ggctgtgcag | ccccagccca | gggcagcaag | catgcccca | tctgtctcct | cacccggagg | 1020 |
| cctctgacca | ccccactcat | gctcagggag | agggtcttct | ggatttttcc | accaggctcc | 1080 |
| gggcagccac | aggctggatg | cccctacccc | aggccctgcg | catacagggg | caggtgctgc | 1140 |
| gctcagacct | gccaagagcc | atatccggga | ggaccctgcc | cctgacctaa | gcccacccca | 1200 |
| aaggccaaac | tctccactcc | ctcagctcag | acaccttctc | tcctcccaga | tctgagtaac | 1260 |
| tcccaatctt | ctctctgcag | agtccaaata | tggtccccca | tgcccatcat | gcccaggtaa | 1320 |
| gccaacccag | gcctcgccct | ccagctcaag | gcgggacagg | tgccctagag | tagcctgcat | 1380 |
| ccagggacag | gccccagccg | ggtgctgacg | catccacctc | catctcttcc | tcagcacctg | 1440 |
| agttcctggg | gggaccatca | gtcttcctgt | tccccccaaa | acccaaggac | actctcatga | 1500 |
| tctcccggac | ccctgaggtc | acgtgcgtgg | tggtggacgt | gagccaggaa | gaccccgagg | 1560 |
| tccagttcaa | ctggtacgtg | gatggcgtgg | aggtgcataa | tgccaagaca | aagccgcggg | 1620 |
| aggagcagtt | caacagcacg | taccgtgtgg | tcagcgtcct | caccgtcctg | caccaggact | 1680 |
| ggctgaacgg | caaggagtac | aagtgcaagg | tctccaacaa | aggcctcccg | tcctccatcg | 1740 |
| agaaaaccat | ctccaaagcc | aaaggtggga | cccacgggt | gcgagggcca | catggacaga | 1800 |
| ggtcagctcg | gcccaccctc | tgccctggga | gtgaccgctg | tgccaacctc | tgtccctaca | 1860 |
| gggcagcccc | gagagccaca | ggtgtacacc | ctgcccccat | cccaggagga | gatgaccaag | 1920 |
| aaccaggtca | gcctgacctg | cctggtcaaa | ggcttctacc | ccagcgacat | cgccgtggag | 1980 |
| tgggagagca | atgggcagcc | ggagaacaac | tacaagacca | cgcctcccgt | gctggactcc | 2040 |
| gacggctcct | tcttcctcta | cagcaggcta | accgtggaca | agagcaggtg | gcaggagggg | 2100 |
| aatgtcttct | catgctccgt | gatgcatgag | gctctgcaca | accactacac | acagaagagc | 2160 |
| ctctcccctgt | ctctgggt | | | | | 2178 |

```
<210> SEQ ID NO 14
<211> LENGTH: 446
<212> TYPE: PRT
<213> ORGANISM: Artificial sequence
<220> FEATURE:
<223> OTHER INFORMATION: Synthetic construct

<400> SEQUENCE: 14

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Ile
            35                  40                  45

Gly Cys Ile Tyr Pro Gly Asn Val Asn Thr Asn Tyr Asn Glu Lys Phe
        50                  55                  60

Lys Asp Arg Ala Thr Leu Thr Val Asp Thr Ser Ile Ser Thr Ala Tyr
 65                  70                  75                  80

Met Glu Leu Ser Arg Leu Arg Ser Asp Thr Ala Val Tyr Phe Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
```

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
        420                 425                 430

His Asn His Tyr Thr Gln Lys Ser Leu Ser Leu Ser Leu Gly
    435                 440                 445

<210> SEQ ID NO 15
<211> LENGTH: 1007
<212> TYPE: DNA
<213> ORGANISM: Artificial sequence
<220> FEATURE:
<223> OTHER INFORMATION: Synthetic construct

<400> SEQUENCE: 15
gacatccaga tgacccagtc tccatcctcc ctgtctgcat ctgtaggaga cagagtcacc     60
atcacttgcc atgccagtca aaacatttat gtttggttaa actggtatca gcagaaacca    120
gggaaagccc ctaagctcct gatctataag gcttccaacc tgcacacagg ggtcccatca    180
aggttcagtg gcagtggatc tgggacagat ttcactctca ccatcagcag tctgcaacct    240
gaagattttg caacttacta ctgtcaacag gtcaaactt atccgtacac gttcggcgga    300
gggaccaagg tggagatcaa acgtgagtcg tacgctagca agcttgatat cgaattctaa    360
actctgaggg ggtcggatga cgtggccatt ctttgcctaa agcattgagt ttactgcaag    420
gtcagaaaag catgcaaagc cctcagaatg gctgcaaaga ctccaacaa acaatttag     480
aactttatta aggaataggg ggaagctagg aagaaactca aacatcaag attttaaata    540
cgcttcttgg tctccttgct ataattatc gggataagca tgctgttttc tgtctgtccc    600
taacatgccc tgtgattatc cgcaaacaac acacccaagg gcagaacttt gttacttaaa    660
caccatcctg tttgcttctt tcctcaggaa ctgtggctgc accatctgtc ttcatcttcc    720
cgccatctga tgagcagttg aaatctggaa ctgcctctgt tgtgtgcctg ctgaataact    780
tctatcccag agaggccaaa gtacagtgga aggtggataa cgccctccaa tcgggtaact    840
cccaggagag tgtcacagag caggacagca aggacagcac ctacagcctc agcagcaccc    900
tgacgctgag caaagcagac tacgagaaac acaaagtcta cgcctgcgaa gtcacccatc    960
agggcctgag ctcgcccgtc acaaagagct tcaacagggg agagtgt                 1007

<210> SEQ ID NO 16
<211> LENGTH: 214
<212> TYPE: PRT
<213> ORGANISM: Artificial sequence
<220> FEATURE:
<223> OTHER INFORMATION: Synthetic construct

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Trp
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Gln Thr Tyr Pro Tyr
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 17
<211> LENGTH: 33
<212> TYPE: DNA
<213> ORGANISM: Artificial sequence
<220> FEATURE:
<223> OTHER INFORMATION: Synthetic construct

<400> SEQUENCE: 17
tcacactacg gcctcgactg gaacttcgat gtc                               33

<210> SEQ ID NO 18
<211> LENGTH: 11
<212> TYPE: PRT
<213> ORGANISM: Artificial sequence
<220> FEATURE:
<223> OTHER INFORMATION: Synthetic construct

<400> SEQUENCE: 18

Ser His Tyr Gly Leu Asp Trp Asn Phe Asp Val
 1                5                  10

<210> SEQ ID NO 19
<211> LENGTH: 51
<212> TYPE: DNA
<213> ORGANISM: Artificial sequence
<220> FEATURE:
<223> OTHER INFORMATION: Synthetic construct

<400> SEQUENCE: 19
tgtatttatc ctggaaatgt caatactaac tataatgaga agttcaagga c            51

<210> SEQ ID NO 20
<211> LENGTH: 17
<212> TYPE: PRT
<213> ORGANISM: Artificial sequence
<220> FEATURE:
<223> OTHER INFORMATION: Synthetic construct

<400> SEQUENCE: 20

Cys Ile Tyr Pro Gly Asn Val Asn Thr Asn Tyr Asn Glu Lys Phe Lys
 1                5                  10                  15
```

Asp

<210> SEQ ID NO 21
<211> LENGTH: 30
<212> TYPE: DNA
<213> ORGANISM: Artificial sequence
<220> FEATURE:
<223> OTHER INFORMATION: Synthetic construct

<400> SEQUENCE: 21
ggatacacct tcaccagcta ctatatacac                                    30

<210> SEQ ID NO 22
<211> LENGTH: 10
<212> TYPE: PRT
<213> ORGANISM: Artificial sequence
<220> FEATURE:
<223> OTHER INFORMATION: Synthetic construct

<400> SEQUENCE: 22

Gly Tyr Thr Phe Thr Ser Tyr Tyr Ile His
1               5                   10

<210> SEQ ID NO 23
<211> LENGTH: 27
<212> TYPE: DNA
<213> ORGANISM: Artificial sequence
<220> FEATURE:
<223> OTHER INFORMATION: Synthetic construct

<400> SEQUENCE: 23
caacagggtc aaacttatcc gtacacg                                       27

<210> SEQ ID NO 24
<211> LENGTH: 9
<212> TYPE: PRT
<213> ORGANISM: Artificial sequence
<220> FEATURE:
<223> OTHER INFORMATION: Synthetic construct

<400> SEQUENCE: 24

Gln Gln Gly Gln Thr Tyr Pro Tyr Thr
1               5

<210> SEQ ID NO 25
<211> LENGTH: 21
<212> TYPE: DNA
<213> ORGANISM: Artificial sequence
<220> FEATURE:
<223> OTHER INFORMATION: Synthetic construct

<400> SEQUENCE: 25
aaggcttcca acctgcacac a                                             21

<210> SEQ ID NO 26
<211> LENGTH: 7
<212> TYPE: PRT
<213> ORGANISM: Artificial sequence
<220> FEATURE:
<223> OTHER INFORMATION: Synthetic construct

<400> SEQUENCE: 26

Lys Ala Ser Asn Leu His Thr
1               5

<210> SEQ ID NO 27
<211> LENGTH: 33

```
<212> TYPE: DNA
<213> ORGANISM: Artificial sequence
<220> FEATURE:
<223> OTHER INFORMATION: Synthetic construct

<400> SEQUENCE: 27
catgccagtc aaaacattta tgtttggtta aac                                      33

<210> SEQ ID NO 28
<211> LENGTH: 11
<212> TYPE: PRT
<213> ORGANISM: Artificial sequence
<220> FEATURE:
<223> OTHER INFORMATION: Synthetic construct

<400> SEQUENCE: 28

His Ala Ser Gln Asn Ile Tyr Val Trp Leu Asn
1               5                   10

<210> SEQ ID NO 29
<211> LENGTH: 2184
<212> TYPE: DNA
<213> ORGANISM: Artificial sequence
<220> FEATURE:
<223> OTHER INFORMATION: Synthetic construct

<400> SEQUENCE: 29
caggtgcagc tggtgcagtc tggggctgag gtgaagaagc ctggggcctc agtgaaggtc         60
tcctgcaagg cttctggata caccttcacc agctactata tacactgggt gcgacaggcc        120
cctggacaag ggcttgagtg gattggatgt atttatcctg gaaatgtcaa tactaactat        180
aatgagaagt tcaaggacag ggccacccct accgtagaca cgtccatcag cacagcctac        240
atggagctga gcaggctgag atctgacgac acggccgtgt atttctgtac aagatcacac        300
tacggcctcg actggaactt cgatgtctgg ggccaaggga ccacggtcac cgtctcctca        360
ggtgagtcgt acgctagcaa gctttctggg gcaggccagg cctgaccttg gctttggggc        420
agggaggggg ctaaggtgag gcaggtggcg ccagccaggt gcacacccaa tgcccatgag        480
cccagacact ggacgctgaa cctcgcggac agttaagaac ccaggggcct ctgcgccctg        540
ggcccagctc tgtcccacac cgcggtcaca tggcaccacc tctcttgcag cctccaccaa        600
gggcccatcg gtcttccccc tggcaccctc ctccaagagc acctctgggg gcacagcggc        660
cctgggctgc ctggtcaagg actacttccc cgaaccggtg acggtgtcgt ggaactcagg        720
cgccctgacc agcggcgtgc acaccttccc ggctgtccta cagtcctcag gactctactc        780
cctcagcagc gtggtgaccg tgccctccag cagcttgggc acccagacct acatctgcaa        840
cgtgaatcac aagcccagca acaccaaggt ggacaagaaa gttggtgaga ggccagcaca        900
gggagggagg gtgtctgctg gaagccaggc tcagcgctcc tgcctggacg catcccggct        960
atgcagcccc agtccagggc agcaaggcag gccccgtctg cctcttcacc cggaggcctc       1020
tgcccgcccc actcatgctc agggagaggg tcttctggct ttttcccagg ctctgggcag       1080
gcacaggcta ggtgcccta acccaggccc tgcacacaaa ggggcaggtg ctgggctcag       1140
acctgccaag agccatatcc gggaggaccc tgcccctgac ctaagcccac ccaaaggcc        1200 aaactctcca ctccctcagc tcggacacct tctctcctcc cagattccag taactcccaa       1260
tcttctctct gcagagccca aatcttgtga caaaactcac acatgcccac cgtgcccagg       1320
taagccagcc caggcctcgc cctccagctc aaggcgggac aggtgcccta gagtagcctg       1380
catccaggga caggccccag ccgggtgctg acacgtccac ctccatctct tcctcagcac       1440
```

```
ctgaactcct gggggaccg tcagtcttcc tcttcccccc aaaacccaag gacaccctca    1500
tgatctcccg gaccctgag gtcacatgcg tggtggtgga cgtgagccac gaagaccctg    1560
aggtcaagtt caactggtac gtggacggcg tggaggtgca taatgccaag acaaagccgc    1620
gggaggagca gtacaacagc acgtaccggg tggtcagcgt cctcaccgtc ctgcaccagg    1680
actggctgaa tggcaaggag tacaagtgca aggtctccaa caaagccctc ccagccccca    1740
tcgagaaaac catctccaaa gccaaaggtg gacccgtgg ggtgcgaggg ccacatggac    1800
agaggccggc tcggcccacc ctctgccctg agagtgaccg ctgtaccaac ctctgtccct    1860
acagggcagc cccgagaacc acaggtgtac accctgcccc catcccggga tgagctgacc    1920
aagaaccagg tcagcctgac ctgcctggtc aaaggcttct atcccagcga catcgccgtg    1980
gagtgggaga gcaatgggca gccggagaac aactacaaga ccacgcctcc cgtgctggac    2040
tccgacggct ccttcttcct ctacagcaag ctcaccgtgg acaagagcag gtggcagcag    2100
gggaacgtct tctcatgctc cgtgatgcat gaggctctgc acaaccacta cacgcagaag    2160
agcctctccc tgtctccggg taaa                                          2184
```

<210> SEQ ID NO 30
<211> LENGTH: 450
<212> TYPE: PRT
<213> ORGANISM: Artificial sequence
<220> FEATURE:
<223> OTHER INFORMATION: Synthetic construct

<400> SEQUENCE: 30

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Cys Ile Tyr Pro Gly Asn Val Asn Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 31
<211> LENGTH: 1007
<212> TYPE: DNA
<213> ORGANISM: Artificial sequence
<220> FEATURE:
<223> OTHER INFORMATION: Synthetic construct

<400> SEQUENCE: 31
gacatccaga tgacccagtc tccatcctcc ctgtctgcat ctgtaggaga cagagtcacc      60
atcacttgcc atgccagtca aaacatttat gtttggttaa actggtatca gcagaaacca     120
gggaaagccc ctaagctcct gatctataag gcttccaacc tgcacacagg ggtcccatca     180
aggttcagtg gcagtggatc tgggacagat tcactctcta ccatcagcag tctgcaacct     240
gaagattttg caacttacta ctgtcaacag ggtcaaactt atccgtacac gttcggcgga     300
gggaccaagg tggagatcaa acgtgagtcg tacgctagca agcttgatat cgaattctaa     360
actctgaggg ggtcggatga cgtggccatt ctttgcctaa agcattgagt ttactgcaag     420
gtcagaaaag catgcaaagc cctcagaatg ctgcaaaga gctccaacaa acaatttag     480
aactttatta aggaataggg ggaagctagg aagaaactca aaacatcaag attttaaata     540
cgcttcttgg tctccttgct ataattatct gggataagca tgctgttttc tgtctgtccc     600
taacatgccc tgtgattatc cgcaaacaac acacccaagg gcagaacttt gttacttaaa     660
caccatcctg tttgcttctt tcctcaggaa ctgtggctgc accatctgtc ttcatcttcc     720
cgccatctga tgagcagttg aaatctggaa ctgcctctgt tgtgtgcctg ctgaataact     780
tctatcccag agaggccaaa gtacagtgga aggtggataa cgcctccaa tcgggtaact     840
```

```
cccaggagag tgtcacagag caggacagca aggacagcac ctacagcctc agcagcaccc    900
tgacgctgag caaagcagac tacgagaaac acaaagtcta cgcctgcgaa gtcacccatc    960
agggcctgag ctcgcccgtc acaaagagct tcaacagggg agagtgt                 1007
```

```
<210> SEQ ID NO 32
<211> LENGTH: 214
<212> TYPE: PRT
<213> ORGANISM: Artificial sequence
<220> FEATURE:
<223> OTHER INFORMATION: Synthetic construct

<400> SEQUENCE: 32
```

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Trp
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 33
<211> LENGTH: 360
<212> TYPE: DNA
<213> ORGANISM: Artificial sequence
<220> FEATURE:
<223> OTHER INFORMATION: Synthetic construct

<400> SEQUENCE: 33
```

```
caggtgcagc tggtgcagtc tggggctgag gtgaagaagc tggggcctc agtgaaggtc      60 tcctgcaagg cttctggata caccttcacc agctactata tacactgggt gcgacaggcc    120
cctggacaag gcttgagtg gattggatgt atttatcctg gaatgtcaa tactaactat      180 aatgagaagt tcaaggacag ggccaccctg accgtagaca cgtccatcag cacagcctac    240
atggagctga gcaggctgag atctgacgac acggccgtgt atttctgtac aagatcacac    300
tacggcctcg actggaactt cgatgtctgg ggccaaggga ccacggtcac cgtctcctca    360
```

<210> SEQ ID NO 34
<211> LENGTH: 120
<212> TYPE: PRT
<213> ORGANISM: Artificial sequence
<220> FEATURE:
<223> OTHER INFORMATION: Synthetic construct

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Cys Ile Tyr Pro Gly Asn Val Asn Thr Asn Tyr Asn Glu Lys Phe
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser
        115                 120

<210> SEQ ID NO 35
<211> LENGTH: 321
<212> TYPE: DNA
<213> ORGANISM: Artificial sequence
<220> FEATURE:
<223> OTHER INFORMATION: Synthetic construct

<400> SEQUENCE: 35
gacatccaga tgacccagtc tccatcctcc ctgtctgcat ctgtaggaga cagagtcacc      60
atcacttgcc atgccagtca aaacatttat gtttggttaa actggtatca gcagaaacca    120
gggaaagccc ctaagctcct gatctataag gcttccaacc tgcacacagg ggtcccatca    180
aggttcagtg gcagtggatc tgggacagat ttcactctca ccatcagcag tctgcaacct    240
gaagattttg caacttacta ctgtcaacag ggtcaaactt atccgtacac gttcggcgga    300
gggaccaagg tggagatcaa a                                              321

<210> SEQ ID NO 36
<211> LENGTH: 107
<212> TYPE: PRT
<213> ORGANISM: Artificial sequence
<220> FEATURE:
<223> OTHER INFORMATION: Synthetic construct

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Trp
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro 65                  70                  75                  80
Glu Asp Phe Ala Thr Tyr Tyr Cys Gln Gln Gly Gln Thr Tyr Pro Tyr
                        85                  90                  95

Thr Phe Gly Gly Gly Thr Lys Val Glu Ile Lys
                100                 105

<210> SEQ ID NO 37
<211> LENGTH: 360
<212> TYPE: DNA
<213> ORGANISM: Artificial sequence
<220> FEATURE:
<223> OTHER INFORMATION: Synthetic construct

<400> SEQUENCE: 37
caggtgcagc tggtgcagtc tggggctgag gtgaagaagc ctggggcctc agtgaaggtc      60
tcctgcaagg cttctggata caccttcacc agctactata tacactgggt gcgacaggcc     120
cctggacaag gccttgagtg gattggatgt atttatcctg gaaatgtcaa tactaactat     180
aatgagaagt tcaaggacag ggccaccctg accgtagaca cgtccatcag cacagcctac     240
atggagctga gcaggctgag atctgacgac acggccgtgt atttctgtac aagatcacac     300
tacggcctcg actggaactt cgatgtctgg ggccaaggga ccacggtcac cgtctcctca     360

<210> SEQ ID NO 38
<211> LENGTH: 120
<212> TYPE: PRT
<213> ORGANISM: Artificial sequence
<220> FEATURE:
<223> OTHER INFORMATION: Synthetic construct

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Ile
            35                  40                  45

Gly Cys Ile Tyr Pro Gly Asn Val Asn Thr Asn Tyr Asn Glu Lys Phe
        50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Trp Asn Phe Asp Val Trp Gly Gln
                100                 105                 110

Gly Thr Thr Val Thr Val Ser Ser
            115                 120

<210> SEQ ID NO 39
<211> LENGTH: 321
<212> TYPE: DNA
<213> ORGANISM: Artificial sequence
<220> FEATURE:
<223> OTHER INFORMATION: Synthetic construct

<400> SEQUENCE: 39
gacatccaga tgacccagtc tccatcctcc ctgtctgcat ctgtaggaga cagagtcacc      60
atcacttgcc atgccagtca aaacatttat gtttggttaa actggtatca gcagaaacca     120
gggaaagccc ctaagctcct gatctataag gcttccaacc tgcacacagg ggtcccatca     180

| | |
|---|---|
| aggttcagtg gcagtggatc tgggacagat ttcactctca ccatcagcag tctgcaacct | 240 |
| gaagattttg caacttacta ctgtcaacag ggtcaaactt atccgtacac gttcggcgga | 300 |
| gggaccaagg tggagatcaa a | 321 |

<210> SEQ ID NO 40
<211> LENGTH: 107
<212> TYPE: PRT
<213> ORGANISM: Artificial sequence
<220> FEATURE:
<223> OTHER INFORMATION: Synthetic construct

<400> SEQUENCE: 40

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Trp
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys
            100                 105
```

<210> SEQ ID NO 41
<211> LENGTH: 2551
<212> TYPE: DNA
<213> ORGANISM: Artificial sequence
<220> FEATURE:
<223> OTHER INFORMATION: Synthetic construct

<400> SEQUENCE: 41

| | |
|---|---|
| ggtaccgggc cgacctcacc atgggatgga gctgtatcat cctcttcttg gtagcaacag | 60 |
| ctacaggtaa ggggctcaca gtagcaggct tgaggtctgg acatatatat gggtgacaat | 120 |
| gacatccact tgcctttct ctccacaggt gtgcattccc aggtgcagct ggtgcagtct | 180 |
| ggggctgagg tgaagaagcc tggggcctca gtgaaggtct cctgcaaggc ttctggatac | 240 |
| accttcacca gctactatat acactgggtg cgacaggccc ctggacaagg gcttgagtgg | 300 |
| attggatgta tttatcctgg aaatgtcaat actaactata tgagaagtt caaggacagg | 360 |
| gccaccctga ccgtagacac gtccatcagc acagcctaca tggagctgag caggctgaga | 420 |
| tctgacgaca cggccgtgta tttctgtaca agatcacact acggcctcga ctggaacttc | 480 |
| gatgtctggg gccaagggac cacggtcacc gtctcctcag gtgagtcgta cgctagcaag | 540 |
| ctttctgggg caggccgggc ctgactttgg ctggggcag ggagggggct aaggtgacgc | 600 |
| aggtggcgcc agccaggtgc acacccaatg cccatgagcc cagacactgg accctgcatg | 660 |
| gaccatcgcg gatagacaag aaccgagggg cctctgcgcc ctgggcccag ctctgtccca | 720 |
| caccgcggtc acatggcacc acctctcttg cagcttccac caagggccca tccgtcttcc | 780 |
| ccctggcgcc ctgctccagg agcacctccg agagcacagc cgccctgggc tgcctggtca | 840 |
| aggactactt ccccgaaccg gtgacggtgt cgtggaactc aggcgccctg accagcggcg | 900 |
| tgcacacctt cccggctgtc ctacagtcct caggactcta ctccctcagc agcgtggtga | 960 |
| ccgtgccctc cagcagcttg ggcacgaaga cctacacctg caacgtagat cacaagccca | 1020 |

```
gcaacaccaa ggtggacaag agagttggtg agaggccagc acaggagggg agggtgtctg    1080
ctggaagcca ggctcagccc tcctgcctgg acgcaccccg gctgtgcagc cccagcccag    1140
ggcagcaagg catgcccat ctgtctcctc acccggaggc ctctgaccac cccactcatg     1200
ctcagggaga gggtcttctg gattttccca ccaggctccg ggcagccaca ggctggatgc    1260
ccctacccca ggccctgcgc atacaggggc aggtgctgcg ctcagacctg ccaagagcca    1320
tatccgggag gaccctgccc ctgacctaag cccacccca aggccaaact ctccactccc     1380
tcagctcaga caccttctct cctcccagat ctgagtaact cccaatcttc tctctgcaga    1440
gtccaaatat ggtccccat gcccatcatg cccaggtaag ccaacccagg cctcgccctc     1500
cagctcaagg cgggacaggt gccctagagt agcctgcatc cagggacagg ccccagccgg    1560
gtgctgacgc atccacctcc atctcttcct cagcacctga gttcctgggg ggaccatcag    1620
tcttcctgtt cccccaaaa cccaaggaca ctctcatgat ctcccggacc cctgaggtca     1680
cgtgcgtggt ggtggacgtg agccaggaag accccgaggt ccagttcaac tggtacgtgg    1740
atggcgtgga ggtgcataat gccaagacaa agccgcggga ggagcagttc aacagcacgt    1800
accgtgtggt cagcgtcctc accgtcctgc accaggactg gctgaacggc aaggagtaca    1860
agtgcaaggt ctccaacaaa ggcctcccgt cctccatcga gaaaaccatc tccaaagcca    1920
aaggtgggac ccacggggtg cgagggccac atggacagag gtcagctcgg cccaccctct    1980
gccctgggag tgaccgctgt gccaacctct gtccctacag ggcagccccg agagccacag    2040
gtgtacaccc tgcccccatc caggaggag atgaccaaga accaggtcag cctgacctgc     2100
ctggtcaaag gcttctaccc cagcgacatc gccgtggagt gggagagcaa tgggcagccg    2160
gagaacaact acaagaccac gcctcccgtg ctggactccg acggctcctt cttcctctac    2220
agcaggctaa ccgtggacaa gagcaggtgg caggagggga atgtcttctc atgctccgtg    2280
atgcatgagg ctctgcacaa ccactacaca cagaagagcc tctccctgtc tctgggtaaa    2340
tgagtgccag ggccggcaag ccccgctcc ccgggctctc ggggtcgcgc gaggatgctt     2400
ggcacgtacc ccgtctacat acttcccagg cacccagcat ggaaataaag cacccaccac    2460
tgccctgggc ccctgtgaga ctgtgatggt tctttccacg ggtcaggccg agtctgaggc    2520
ctgagtgaca tgagggaggc agagcggatc c                                   2551
```

<210> SEQ ID NO 42
<211> LENGTH: 466
<212> TYPE: PRT
<213> ORGANISM: Artificial sequence
<220> FEATURE:
<223> OTHER INFORMATION: Synthetic construct

<400> SEQUENCE: 42

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Tyr Ile His Trp Val Arg Gln Ala Pro Gly Gln Gly Leu
    50                  55                  60

Glu Trp Ile Gly Cys Ile Tyr Pro Gly Asn Val Asn Thr Asn Tyr Asn
65                  70                  75                  80

Glu Lys Phe Lys Asp Arg Ala Thr Leu Thr Val Asp Thr Ser Ile Ser
                85                  90                  95
```

Thr Ala Tyr Met Glu Leu Ser Arg Leu Arg Ser Asp Asp Thr Ala Val
                100                 105                 110

Tyr Phe Cys Thr Arg Ser His Tyr Gly Leu Asp Trp Asn Phe Asp Val
            115                 120                 125

Trp Gly Gln Gly Thr Thr Val Thr Val Ser Ser Ala Ser Thr Lys Gly
        130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
210                 215                 220

Asp His Lys Pro Ser Asn Thr Lys Val Asp Lys Arg Val Glu Ser Lys
225                 230                 235                 240

Tyr Gly Pro Pro Cys Pro Ser Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
450                 455                 460

Gly Lys
465

<210> SEQ ID NO 43
<211> LENGTH: 1721
<212> TYPE: DNA
<213> ORGANISM: Artificial sequence
<220> FEATURE:
<223> OTHER INFORMATION: Synthetic construct

<400> SEQUENCE: 43

```
ggtaccgggc cgacctcacc atgggatgga gctgtatcat cctcttcttg gtagcaacag      60
ctacaggtaa ggggctcaca gtagcaggct gaggtctgg acatatatat gggtgacaat      120
gacatccact ttgcctttct ctccacaggt gtgcattccg acatccagat gacccagtct      180
ccatcctccc tgtctgcatc tgtaggagac agagtcacca tcacttgcca tgccagtcaa      240
aacatttatg tttggttaaa ctggtatcag cagaaaccag ggaaagcccc taagctcctg      300
atctataagg cttccaacct gcacacaggg gtcccatcaa ggttcagtgg cagtggatct      360
gggacagatt tcactctcac catcagcagt ctgcaacctg aagattttgc aacttactac      420
tgtcaacagg gtcaaactta tccgtacacg ttcggcggag ggaccaaggt ggagatcaaa      480
cgtgagtcgt acgctagcaa gcttgatatc gaattctaaa ctctgagggg gtcggatgac      540
gtggccattc tttgcctaaa gcattgagtt tactgcaagg tcagaaaagc atgcaaagcc      600
ctcagaatgg ctgcaaagag ctccaacaaa acaatttaga actttattaa ggaatagggg      660
gaagctagga agaaactcaa acatcaagat ttttaaatac gcttcttggt ctccttgcta      720
taattatctg gataagcat gctgtttct gtctgtccct aacatgccct gtgattatcc      780
gcaaacaaca cacccaaggg cagaactttg ttacttaaac accatcctgt ttgcttcttt      840
cctcaggaac tgtggctgca ccatctgtct tcatcttccc gccatctgat gagcagttga      900
aatctggaac tgcctctgtt gtgtgcctgc tgaataactt ctatcccaga gaggccaaag      960
tacagtggaa ggtggataac gccctccaat cgggtaactc ccaggagagt gtcacagagc     1020
aggacagcaa ggacagcacc tacagcctca gcagcaccct gacgctgagc aaagcagact     1080
acgagaaaca caaagtctac gcctgcgaag tcacccatca gggcctgagc tcgcccgtca     1140
caaagagctt caacagggga gagtgttaga gggagaagtg cccccacctg ctcctcagtt     1200
ccagcctgac cccctcccat cctttggcct ctgacccttt ttccacaggg gacctacccc     1260
tattgcggtc ctccagctca tctttcacct cacccccctc ctcctccttg gctttaatta     1320
tgctaatgtt ggaggagaat gaataaataa agtgaatctt tgcacctgtg gtttctctct     1380
ttcctcattt aataattatt atctgttgtt ttaccaacta ctcaatttct cttataaggg     1440
actaaatatg tagtcatcct aaggcgcata accatttata aaaatcatcc ttcattctat     1500
tttaccctat catcctctgc aagacagtcc tccctcaaac ccacaagcct tctgtcctca     1560
cagtcccctg ggccatggta ggagagactt gcttccttgt tttccctcc tcagcaagcc     1620
ctcatagtcc tttttaaggg tgacaggtct tacagtcata tatcctttga ttcaattccc     1680
tgagaatcaa ccaaagcaaa ttcctgcagc ccgggggatc c                         1721
```

<210> SEQ ID NO 44
<211> LENGTH: 233
<212> TYPE: PRT
<213> ORGANISM: Artificial sequence
<220> FEATURE:
<223> OTHER INFORMATION: Synthetic construct

<400> SEQUENCE: 44

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys His Ala Ser Gln Asn Ile
        35                  40                  45
```

```
Tyr Val Trp Leu Asn Trp Tyr Gln Gln Lys Pro Gly Lys Ala Pro Lys
 50                  55                  60

Leu Leu Ile Tyr Lys Ala Ser Asn Leu His Thr Gly Val Pro Ser Arg
 65                  70                  75                  80

Phe Ser Gly Ser Gly Ser Gly Thr Asp Phe Thr Leu Thr Ile Ser Ser
                 85                  90                  95

Leu Gln Pro Glu Asp Phe Ala Thr Tyr Tyr Cys Gln Gln Gly Gln Thr
                100                 105                 110

Tyr Pro Tyr Thr Phe Gly Gly Gly Thr Lys Val Glu Ile Lys Arg Thr
                115                 120                 125

Val Ala Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
                180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 45
<211> LENGTH: 2553
<212> TYPE: DNA
<213> ORGANISM: Artificial sequence
<220> FEATURE:
<223> OTHER INFORMATION: Synthetic construct

<400> SEQUENCE: 45

```
ggtaccgggc cgacctcacc atgggatgga gctgtatcat cctcttcttg gtagcaacag      60
ctacaggtaa ggggctcaca gtagcaggct tgaggtctgg acatatatat gggtgacaat     120
gacatccact ttgcctttct ctccacaggt gtgcattccc aggtgcagct ggtgcagtct     180
ggggctgagg tgaagaagcc tggggcctca gtgaaggtct cctgcaaggc ttctggatac     240
accttcacca gctactatat acactgggtg cgacaggccc tggacaaggg cttgagtgg     300 attggatgta tttatcctgg aaatgtcaat actaactata tgagaagtt caaggacagg     360 gccaccctga ccgtagacac gtccatcagc acagcctaca tggagctgag caggctgaga     420
tctgacgaca cggccgtgta tttctgtaca agatcacact acggcctcga ctggaacttc     480
gatgtctggg gccaagggac cacggtcacc gtctcctcag gtgagtcgta cgctagcaag     540
ctttctgggg caggccaggc ctgaccttgg ctttggggca gggagggggc taaggtgagg     600
caggtggcgc cagccaggtg cacacccaat gcccatgagc ccagacactg gacgctgaac     660
ctcgcggaca gttaagaacc caggggcctc tgcgccctgg gccagctct gtcccacacc     720 gcggtcacat ggcaccacct tcttgcagc ctccaccaag ggcccatcgg tcttccccct     780
ggcaccctcc tccaagagca cctctggggg cacagcggcc ctgggctgcc tggtcaagga     840
ctacttcccc gaaccggtga cggtgtcgtg gaactcaggc gccctgacca gcggcgtgca     900
caccttcccg gctgtcctac agtcctcagg actctactcc ctcagcagcg tggtgaccgt     960
gccctccagc agcttgggca cccagaccta catctgcaac gtgaatcaca agcccagcaa    1020
```

```
caccaaggtg acaagaaag ttggtgagag gccagcacag ggagggaggg tgtctgctgg    1080
aagccaggct cagcgctcct gcctggacgc atcccggcta tgcagcccca gtccagggca    1140
gcaaggcagg ccccgtctgc ctcttcaccc ggaggcctct gcccgcccca ctcatgctca    1200
gggagagggt cttctggctt tttcccaggc tctgggcagg cacaggctag gtgcccctaa    1260
cccaggccct gcacacaaag gggcaggtgc tgggctcaga cctgccaaga gccatatccg    1320
ggaggaccct gccctgacc taagcccacc ccaaaggcca aactctccac tccctcagct    1380
cggacacctt ctctcctccc agattccagt aactcccaat cttctctctg cagagcccaa    1440
atcttgtgac aaaactcaca catgcccacc gtgcccaggt aagccagccc aggcctcgcc    1500
ctccagctca aggcgggaca ggtgccctag agtagcctgc atccagggac aggccccagc    1560
cgggtgctga cacgtccacc tccatctctt cctcagcacc tgaactcctg ggggaccgt    1620 cagtcttcct cttccccca aacccaagg acaccctcat gatctcccgg acccctgagg    1680
tcacatgcgt ggtggtggac gtgagccacg aagaccctga ggtcaagttc aactggtacg    1740
tggacggcgt ggaggtgcat aatgccaaga caaagccgcg ggaggagcag tacaacagca    1800
cgtaccgggt ggtcagcgtc ctcaccgtcc tgcaccagga ctggctgaat ggcaaggagt    1860
acaagtgcaa ggtctccaac aaagccctcc cagcccccat cgagaaaacc atctccaaag    1920
ccaaaggtgg acccgtgggg gtgcgagggc acatggacag gaggccggct cggcccaccc    1980
tctgccctga gagtgaccgc tgtaccaacc tctgtcccta cagggcagcc ccgagaacca    2040
caggtgtaca ccctgccccc atcccgggat gagctgacca gaaccaggt cagcctgacc    2100 tgcctggtca aaggcttcta tcccagcgac atcgccgtgg agtgggagag caatgggcag    2160
ccggagaaca actacaagac cacgcctccc gtgctggact ccgacggctc cttcttcctc    2220
tacagcaagc tcaccgtgga caagagcagg tggcagcagg ggaacgtctt ctcatgctcc    2280
gtgatgcatg aggctctgca caaccactac acgcagaaga gcctctccct gtctccgggt    2340
aaatgagtgc gacggccggc aagcccccgc tccccgggct ctcgcggtcg cacgaggatg    2400
cttggcacgt accccctgta catacttccc gggcgcccag catggaaata aagcacccag    2460
cgctgccctg ggccctgcg agactgtgat ggttctttcc acgggtcagg ccgagtctga    2520
ggcctgagtg gcatgaggga ggcagagcgg gtc                                2553
```

<210> SEQ ID NO 46
<211> LENGTH: 469
<212> TYPE: PRT
<213> ORGANISM: Artificial sequence
<220> FEATURE:
<223> OTHER INFORMATION: Synthetic construct

<400> SEQUENCE: 46

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Tyr Ile His Trp Val Arg Gln Ala Pro Gly Gln Gly Leu
    50                  55                  60

Glu Trp Ile Gly Cys Ile Tyr Pro Gly Asn Val Asn Thr Asn Tyr Asn
65                  70                  75                  80

Glu Lys Phe Lys Asp Arg Ala Thr Leu Thr Val Asp Thr Ser Ile Ser
                85                  90                  95
```

```
Thr Ala Tyr Met Glu Leu Ser Arg Leu Arg Ser Asp Asp Thr Ala Val
                100                 105                 110
Tyr Phe Cys Thr Arg Ser His Tyr Gly Leu Asp Trp Asn Phe Asp Val
            115                 120                 125
Trp Gly Gln Gly Thr Thr Val Thr Val Ser Ser Ala Ser Thr Lys Gly
130                 135                 140
Pro Ser Val Phe Pro Leu Ala Pro Ser Ser Lys Ser Thr Ser Gly Gly
145                 150                 155                 160
Thr Ala Ala Leu Gly Cys Leu Val Lys Asp Tyr Phe Pro Glu Pro Val
                165                 170                 175
Thr Val Ser Trp Asn Ser Gly Ala Leu Thr Ser Gly Val His Thr Phe
            180                 185                 190
Pro Ala Val Leu Gln Ser Ser Gly Leu Tyr Ser Leu Ser Ser Val Val
        195                 200                 205
Thr Val Pro Ser Ser Ser Leu Gly Thr Gln Thr Tyr Ile Cys Asn Val
    210                 215                 220
Asn His Lys Pro Ser Asn Thr Lys Val Asp Lys Lys Val Glu Pro Lys
225                 230                 235                 240
Ser Cys Asp Lys Thr His Thr Cys Pro Pro Cys Pro Ala Pro Glu Leu
                245                 250                 255
Leu Gly Gly Pro Ser Val Phe Leu Phe Pro Pro Lys Pro Lys Asp Thr
            260                 265                 270
Leu Met Ile Ser Arg Thr Pro Glu Val Thr Cys Val Val Val Asp Val
        275                 280                 285
Ser His Glu Asp Pro Glu Val Lys Phe Asn Trp Tyr Val Asp Gly Val
    290                 295                 300
Glu Val His Asn Ala Lys Thr Lys Pro Arg Glu Glu Gln Tyr Asn Ser
305                 310                 315                 320
Thr Tyr Arg Val Val Ser Val Leu Thr Val Leu His Gln Asp Trp Leu
                325                 330                 335
Asn Gly Lys Glu Tyr Lys Cys Lys Val Ser Asn Lys Ala Leu Pro Ala
            340                 345                 350
Pro Ile Glu Lys Thr Ile Ser Lys Ala Lys Gly Gln Pro Arg Glu Pro
        355                 360                 365
Gln Val Tyr Thr Leu Pro Pro Ser Arg Asp Glu Leu Thr Lys Asn Gln
    370                 375                 380
Val Ser Leu Thr Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
                405                 410                 415
Pro Pro Val Leu Asp Ser Asp Gly Ser Phe Phe Leu Tyr Ser Lys Leu
            420                 425                 430
Thr Val Asp Lys Ser Arg Trp Gln Gln Gly Asn Val Phe Ser Cys Ser
        435                 440                 445
Val Met His Glu Ala Leu His Asn His Tyr Thr Gln Lys Ser Leu Ser
    450                 455                 460
Leu Ser Pro Gly Lys
465

<210> SEQ ID NO 47
<211> LENGTH: 1721
<212> TYPE: DNA
<213> ORGANISM: Artificial sequence
<220> FEATURE:
<223> OTHER INFORMATION: Synthetic construct
```

-continued

```
<400> SEQUENCE: 47
ggtaccgggc cgacctcacc atgggatgga gctgtatcat cctcttcttg gtagcaacag      60
ctacaggtaa ggggctcaca gtagcaggct tgaggtctgg acatatatat gggtgacaat     120
gacatccact ttgcctttct ctccacaggt gtgcattccg acatccagat gacccagtct     180
ccatcctccc tgtctgcatc tgtaggagac agagtcacca tcacttgcca tgccagtcaa     240
aacatttatg tttggttaaa ctggtatcag cagaaaccag ggaaagcccc taagctcctg     300
atctataagg cttccaacct gcacacaggg gtcccatcaa ggttcagtgg cagtggatct     360
gggacagatt tcactctcac catcagcagt ctgcaacctg aagattttgc aacttactac     420
tgtcaacagg gtcaaactta tccgtacacg ttcggcggag ggaccaaggt ggagatcaaa     480
cgtgagtcgt acgctagcaa gcttgatatc gaattctaaa ctctgagggg gtcggatgac     540
gtggccattc tttgcctaaa gcattgagtt tactgcaagg tcagaaaagc atgcaaagcc     600
ctcagaatgg ctgcaaagag ctccaacaaa acaatttaga actttattaa ggaatagggg     660
gaagctagga agaaactcaa aacatcaaga ttttaaatac gcttcttggt ctccttgcta     720
taattatctg ggataagcat gctgttttct gtctgtccct aacatgccct gtgattatcc     780
gcaaacaaca cacccaaggg cagaactttg ttacttaaac accatcctgt ttgcttcttt     840
cctcaggaac tgtggctgca ccatctgtct tcatcttccc gccatctgat gagcagttga     900
aatctggaac tgcctctgtt gtgtgcctgc tgaataactt ctatcccaga gaggccaaag     960
tacagtggaa ggtggataac gcctccaat cgggtaactc ccaggagagt gtcacagagc    1020
aggacagcaa ggacagcacc tacagcctca gcagcaccct gacgctgagc aaagcagact    1080
acgagaaaca caaagtctac gcctgcgaag tcacccatca gggcctgagc tcgcccgtca    1140
caaagagctt caacagggga gagtgttaga gggagaagtg cccccacctg ctcctcagtt    1200
ccagcctgac cccctcccat cctttggcct ctgacccttt ttccacaggg gacctacccc    1260
tattgcggtc ctccagctca tctttcacct caccccccctc ctcctccttg gctttaatta    1320
tgctaatgtt ggaggagaat gaataaataa agtgaatctt tgcacctgtg gtttctctct    1380
ttcctcattt aataattatt atctgttgtt ttaccaacta ctcaatttct cttataaggg    1440
actaaatatg tagtcatcct aaggcgcata accatttata aaaatcatcc ttcattctat    1500
tttaccctat catcctctgc aagacagtcc tccctcaaac ccacaagcct tctgtcctca    1560
cagtcccctg ggccatggta ggagagactt gcttccttgt tttcccctcc tcagcaagcc    1620
ctcatagtcc ttttttaaggg tgacaggtct tacagtcata tatcctttga ttcaattccc    1680
tgagaatcaa ccaaagcaaa ttcctgcagc ccggggggatc                          1721
```

```
<210> SEQ ID NO 48
<211> LENGTH: 233
<212> TYPE: PRT
<213> ORGANISM: Artificial sequence
<220> FEATURE:
<223> OTHER INFORMATION: Synthetic construct

<400> SEQUENCE: 48

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys His Ala Ser Gln Asn Ile
        35                  40                  45

Tyr Val Trp Leu Asn Trp Tyr Gln Gln Lys Pro Gly Lys Ala Pro Lys
```

-continued

```
                50                  55                  60
Leu Leu Ile Tyr Lys Ala Ser Asn Leu His Thr Gly Val Pro Ser Arg
 65              70                  75                  80

Phe Ser Gly Ser Gly Ser Gly Thr Asp Phe Thr Leu Thr Ile Ser Ser
                 85                  90                  95

Leu Gln Pro Glu Asp Phe Ala Thr Tyr Tyr Cys Gln Gln Gly Gln Thr
                100                 105                 110

Tyr Pro Tyr Thr Phe Gly Gly Gly Thr Lys Val Glu Ile Lys Arg Thr
            115                 120                 125

Val Ala Ala Pro Ser Val Phe Ile Phe Pro Pro Ser Asp Glu Gln Leu
            130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
                180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
            210                 215                 220

Thr Lys Ser Phe Asn Arg Gly Glu Cys
225                 230
```